(12) United States Patent
Tochio et al.

(10) Patent No.: US 9,725,748 B2
(45) Date of Patent: Aug. 8, 2017

(54) METHOD FOR PRODUCING FRUCTOSE-ADDED CARBOHYDRATE

(71) Applicants: B FOOD SCIENCE CO., LTD., Chita-shi (JP); MICROBIOPHARM JAPAN CO., LTD., Chuo-ku (JP)

(72) Inventors: Takumi Tochio, Chita (JP); Naomi Ito, Chita (JP); Saki Nakamura, Chita (JP); Tadashi Fujii, Chuo-ku (JP); Keisuke Tamura, Chuo-ku (JP)

(73) Assignees: Microbiopharm Japan Co., Ltd., Tokyo (JP); B Food Science Co., Ltd., Aichi (JP)

( * ) Notice: Subject to any disclaimer, the term of this patent is extended or adjusted under 35 U.S.C. 154(b) by 0 days.

(21) Appl. No.: 15/107,819

(22) PCT Filed: Dec. 26, 2014

(86) PCT No.: PCT/JP2014/084685
§ 371 (c)(1),
(2) Date: Jun. 23, 2016

(87) PCT Pub. No.: WO2015/099169
PCT Pub. Date: Jul. 2, 2015

(65) Prior Publication Data
US 2016/0319316 A1    Nov. 3, 2016

(30) Foreign Application Priority Data

Dec. 27, 2013  (JP) ................................. 2013-273402
Aug. 1, 2014  (JP) ................................. 2014-158037

(51) Int. Cl.
| | |
|---|---|
| C12N 9/26 | (2006.01) |
| C12N 1/20 | (2006.01) |
| C12N 15/00 | (2006.01) |
| C12P 21/06 | (2006.01) |
| C12P 21/04 | (2006.01) |
| C07H 21/04 | (2006.01) |
| C12P 19/02 | (2006.01) |
| C12P 21/00 | (2006.01) |
| C12P 19/14 | (2006.01) |
| C12N 15/70 | (2006.01) |

(52) U.S. Cl.
CPC ............ *C12P 19/02* (2013.01); *C12N 9/2431* (2013.01); *C12N 15/70* (2013.01); *C12P 19/14* (2013.01); *C12P 21/00* (2013.01); *C12Y 302/01026* (2013.01); *C07K 2319/01* (2013.01)

(58) Field of Classification Search
CPC ......................... C12N 9/2431; C07K 2319/01
See application file for complete search history.

(56) References Cited

U.S. PATENT DOCUMENTS 6,566,111 B1    5/2003  Yanai et al.

FOREIGN PATENT DOCUMENTS

| CN | 1276008 A | 12/2000 |
|---|---|---|
| JP | H08-47394 A | 2/1996 |
| JP | H10-504182 | 4/1998 |
| JP | 2004-222573 A | 8/2004 |
| JP | 2005-312426 A | 11/2005 |
| JP | 2006-067958 A | 3/2006 |
| JP | 2009-207364 A | 9/2009 |
| JP | 2013-252056 A | 12/2013 |
| WO | WO 95/33838 | 12/1995 |

OTHER PUBLICATIONS

Machine Translation of JP 2013-252056. Retrieved from AIPN on Sep. 15, 2016 via https://dossier1.j-platpat.inpit.go.jp/tri/all/odse/ODSE_GM101_Top.action.*
Uppenberg. The sequence, crystal structure determination and refinement of two crystal forms of lipase B from Candida antarctica. Structure 2:293-308. 1994.*
Beta-Fructofuranosidase. UnitProtKB database. Retrieved in Oct. 27, 2016 via http://www.uniprot.org/uniprot/?query=aspergillus++beta+fructofuranosidase&sort=score.*
Eppinger. D5DB84. UniProtKB Database. Oct. 2013.*
Candela. Poly-gamma-glutamate in bacteria. Molecular Microbiology (2006) 60 (5), 1091-1098.*
Branden et al. Introduction to Protein Structure, Garland Publishing Inc., New York, p. 247, 1991.*
Japanese Office Action for Japanese Patent Application No. 2014-158037 dated Aug. 26, 2015 (with English Translation).
Narita et al., Appl. Microbiol. Biothechnol., 70(5):564-72 (2006).
PCT/JP2014/084685 International Search Report issued by Japanese Patent Office Mar. 24, 2015.
Ashiuchi et al., Appl. Microbiol. Biothechnol., 59:9-14 (2002).
Extended European Search Report for Application No. EP 14 87 4014 issued by European Patent Office dated Jun. 7, 2017.
Goldman et al., J. of Biological Chemistry, 283(47):32209-217 (2008).
Jung et al., Nature Biotechnology, 16(6):576-80, (1998).

* cited by examiner

*Primary Examiner* — Yong Pak
(74) *Attorney, Agent, or Firm* — RatnerPrestia

(57) ABSTRACT

[Problem]
To provide a production method capable of simply and efficiently producing a fructose-added carbohydrate using β-fructofuranosidase.
[Solution]
A method for producing a fructose-added carbohydrate, said method having a step in which a receptor substrate and a hydrate containing terminal fructose residue are brought into contact with:
  *Escherichia coli* expressing an anchor protein for expression on a cell surface and β-fructofuranosidase as one polypeptide,
  a composition including dead cells of the expressing *Escherichia coli*, or
  a polypeptide obtained from the expressing *Escherichia coli* and including an amino acid sequence of β-fructofuranosidase.

3 Claims, 3 Drawing Sheets

[Figure 1]
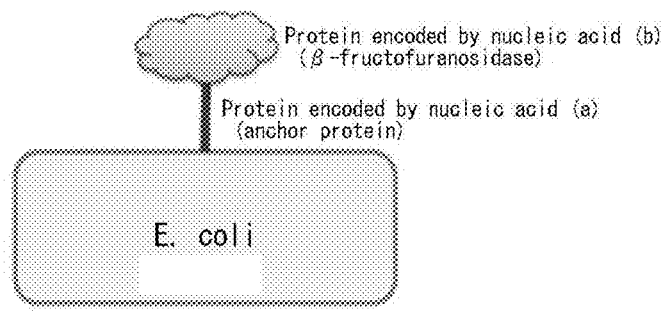
[Figure 2]
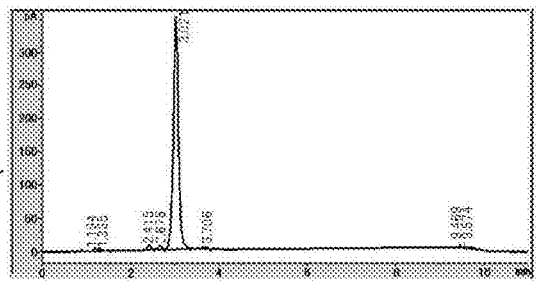
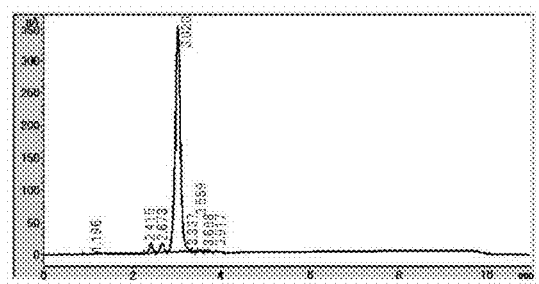

[Figure 3]
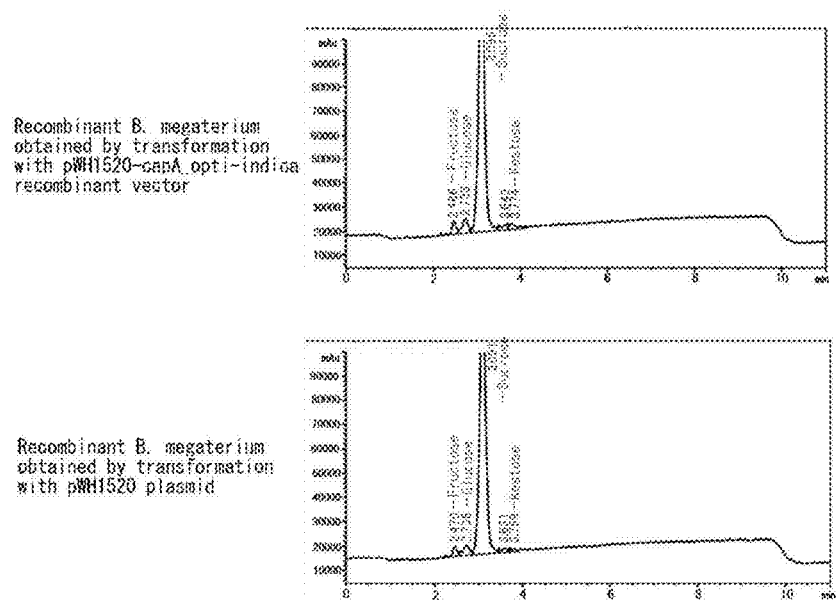

[Figure 4]
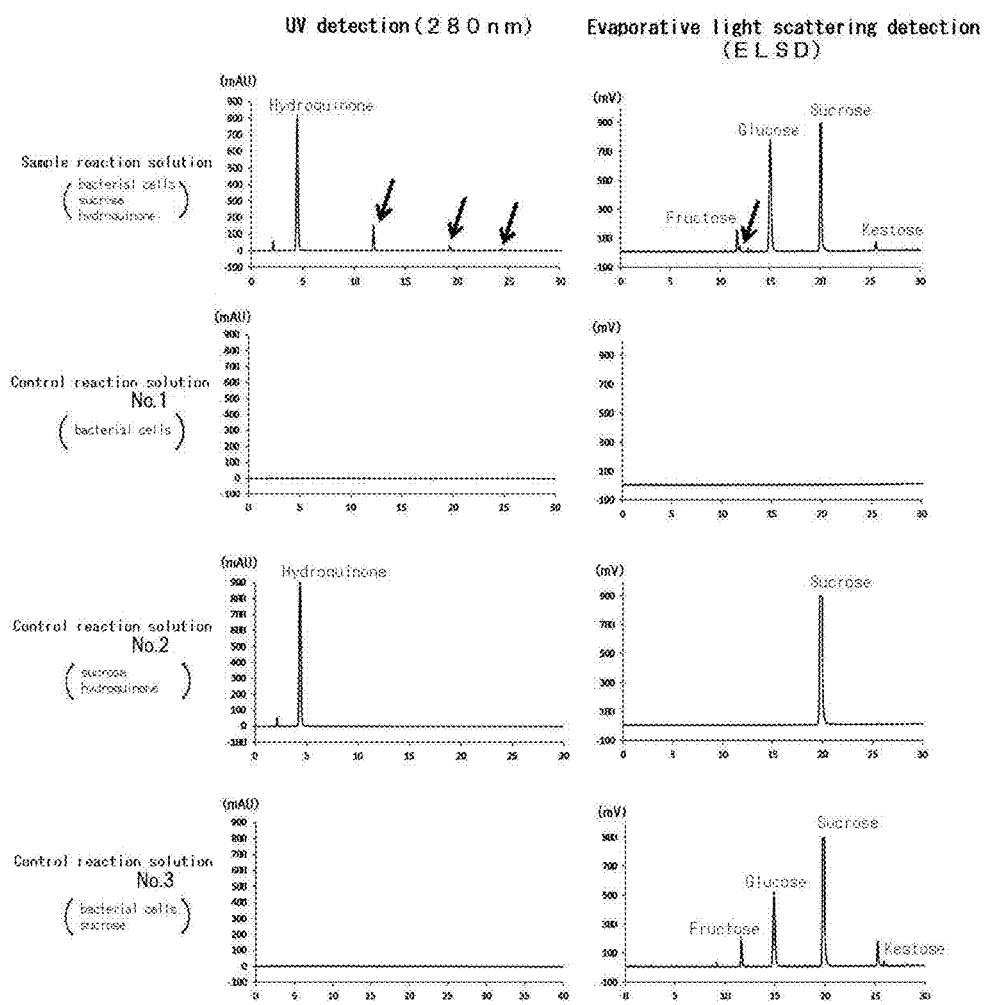

METHOD FOR PRODUCING FRUCTOSE-ADDED CARBOHYDRATE

CROSS-REFERENCE TO RELATED APPLICATIONS

This application is a U.S. National Phase Application of PCT International Application PCT/JP2014/084685, filed Dec. 26, 2014 which claims priority to Japanese Application No. 2013-273402, filed Dec. 27, 2013, and Japanese Application No. 2014-158037, filed Aug. 1, 2014, the contents of which are incorporated herein by reference in their entireties for all purposes.

TECHNICAL FIELD

The present invention relates to a method for producing a fructose-added carbohydrate and particularly relates to a production method capable of efficiently producing a fructose-added carbohydrate using a β-fructofuranosidase, and E. coli, a composition and a polypeptide that can be used in the production method, and a fructose-added carbohydrate produced by the production method.

BACKGROUND OF THE INVENTION

β-fructofuranosidases are enzymes that recognize fructose in a carbohydrate containing a terminal fructose residue and hydrolyze the bond at the fructose residue. Some β-fructofuranosidases have the activity of transferring fructose resulting from the hydrolysis to a receptor substrate. Specifically, fructose can be transferred to a carbohydrate or a non-carbohydrate substance using such a β-fructofuranosidase having this activity to produce a fructose-added carbohydrate.

Heretofore, for example, a method which involves contacting a sugar substrate with a carrier on which hyphae of koji mold carrying a β-fructofuranosidase are immobilized (Patent Literature 1) and a method using levansucrase derived from Zymomonas mobilis or extracellular invertase (Patent Literature 2) have each been disclosed as a method for producing a fructose-added carbohydrate using a β-fructofuranosidase.

CITATION LIST

Patent Literature

Patent Literature 1: Japanese Patent Laid-Open No. 2013-252056
Patent Literature 2: Japanese Patent Laid-Open No. 2006-67958

SUMMARY OF THE INVENTION

Technical Problem

However, the method described in Patent Literature 1 is a method for producing an oligosaccharide by immobilizing hyphae of koji mold intrinsically having a β-fructofuranosidase onto a carrier such as diatomaceous earth or perlite and thus has difficulty in conveniently and efficiently producing an oligosaccharide using a foreign β-fructofuranosidase. This is because the production of an oligosaccharide by this method using the transfer of a foreign β-fructofuranosidase requires deactivating the endogenous β-fructofuranosidase of the koji mold in advance for accurate evaluation, leading to poor handleability. Similarly, the method described in Patent Literature 2 is a method for producing a fructose glycoside using a β-fructofuranosidase derived from Zymomonas mobilis and thus is not a method capable of producing a fructose glycoside irrespective of the origin of a β-fructofuranosidase.

The present invention has been made to solve these problems, and an object of the present invention is to provide a production method capable of efficiently and conveniently producing a fructose-added carbohydrate, irrespective of the origin of a β-fructofuranosidase, by the expression of a foreign β-fructofuranosidase in E. coli, which facilitates evaluating the activity of the introduced β-fructofuranosidase because of intrinsically having no β-fructofuranosidase and is easily handled in transformation or culture. And an object of the present invention is to provide E. coli, a composition and a polypeptide that can be used in the production method, and a fructose-added carbohydrate produced by the production method.

Solution to Problem

The present inventors have conducted diligent studies and consequently completed the following aspects of the invention by finding that a fructose-added carbohydrate can be produced efficiently and conveniently by using E. coli caused to express an anchor protein for expression on the cell surface and a β-fructofuranosidase as one polypeptide.

(1) A method for producing a fructose-added carbohydrate according to the present invention comprises a step of contacting a carbohydrate containing a terminal fructose residue and a receptor substrate with E. coli expressing the following nucleic acids (a) and (b) as one polypeptide, a composition comprising dead cells of the expressing E. coli, or a polypeptide obtained from the expressing E. coli and comprising an amino acid sequence encoded by the nucleic acid (b): (a) a nucleic acid encoding an amino acid sequence having 45% or higher identity to an amino acid sequence of PgsA protein represented by SEQ ID NO: 6 or an amino acid sequence of CapA protein represented by SEQ ID NO: 34, and (b) a nucleic acid encoding an amino acid sequence of a β-fructofuranosidase.

(2) E. coli according to the present invention is E. coli expressible of or expressing the following nucleic acids (a) and (b) as one polypeptide: (a) a nucleic acid encoding an amino acid sequence having 45% or higher identity to an amino acid sequence of PgsA protein represented by SEQ ID NO: 6 or an amino acid sequence of CapA protein represented by SEQ ID NO: 34, and (b) a nucleic acid encoding an amino acid sequence of a β-fructofuranosidase.

(3) A composition according to the present invention is a composition comprising dead cells of E. coli expressing the following nucleic acids (a) and (b) as one polypeptide: (a) a nucleic acid encoding an amino acid sequence having 45% or higher identity to an amino acid sequence of PgsA protein represented by SEQ ID NO: 6 or an amino acid sequence of CapA protein represented by SEQ ID NO: 34, and (b) a nucleic acid encoding an amino acid sequence of a β-fructofuranosidase.

(4) A polypeptide according to the present invention is a polypeptide obtained from E. coli expressing the following nucleic acids (a) and (b) as one polypeptide, and comprising an amino acid sequence encoded by the nucleic acid (b): (a) a nucleic acid encoding an amino acid sequence having 45% or higher identity to an amino acid sequence of PgsA protein represented by SEQ ID NO: 6 or an amino acid sequence of CapA protein represented by SEQ ID NO: 34, and (b) a nucleic acid encoding an amino acid sequence of a β-fructofuranosidase.

(5) A fructose-added carbohydrate according to the present invention is a fructose-added carbohydrate produced by the production method according to (1).

Advantageous Effects of Invention

According to the method for producing a fructose-added carbohydrate according to the present invention, or the *E. coli*, the composition or the polypeptide that can be used in the production method, a fructose-added carbohydrate can be produced conveniently and efficiently using any of β-fructofuranosidases derived from various organisms.

BRIEF DESCRIPTION OF THE DRAWINGS

FIG. 1 is a diagram schematically showing one embodiment of the "*E. coli* expressing the nucleic acids (a) and (b) as one polypeptide" according to the present invention.

FIG. 2 is an HPLC chart showing saccharide composition in a reaction solution obtained by contacting a 45% sucrose solution with recombinant *B. subtilis* obtained by transformation with a pHT43-pgsA-*indica* recombinant vector or a pHT43 plasmid.

FIG. 3 is an HPLC chart showing saccharide composition in a reaction solution obtained by contacting a 45% sucrose solution with recombinant *B. megaterium* obtained by transformation with a pWH1520-capA_opti-*indica* recombinant vector or a pWH1520 plasmid.

FIG. 4 is an HPLC chart showing substance composition in a reaction solution (sample reaction solution) obtained by contacting hydroquinone as a receptor substrate and sucrose as a donor substrate with recombinant *E. coli* obtained by transformation with a pCDF-pgsA-*indica* recombinant vector, and various control reaction solutions (control reaction solution Nos. 1 to 3).

DETAILED DESCRIPTION OF THE INVENTION

Hereinafter, the method for producing a fructose-added carbohydrate according to the present invention, and the *E. coli*, the composition and the polypeptide that can be used in the production method, and the fructose-added carbohydrate produced by the production method will be described in detail.

In the present invention, the "carbohydrate" includes a compound represented by $C_n(H_2O)_m$ as well as an aldehyde or ketone derivative of a polyhydric alcohol, and a relative derivative or condensation product thereof. Specifically, the "carbohydrate" according to the present invention includes a monosaccharide, an oligosaccharide, and a polysaccharide as well as complex carbohydrates composed of these saccharides covalently bonded to proteins, lipids, or the like, and a glycoside composed of an aglycone (e.g., alcohols, phenols, saponins, and dyes) bonded to a reducing group of a monosaccharide or an oligosaccharide (Iwanami Biological Dictionary, 4th edition; published by Iwanami Shoten, Publishers, 2005). The "carbohydrate" according to the present invention may be used interchangeably with "saccharide", "sugar", etc.

In the present invention, the "fructose-added carbohydrate" refers to a compound containing one or more fructose residues as a constituent. Specific examples of the "fructose-added carbohydrate" according to the present invention can include: disaccharides composed of fructose bonded to a monosaccharide other than fructose; oligosaccharides containing a fructose residue, such as nystose and kestose; polysaccharides containing a fructose residue; sugar alcohols containing a fructose residue; and glycosides composed of fructose bonded to a non-saccharide substance (aglycone).

In the present invention, the oligosaccharide refers to a saccharide comprising approximately 3 to a dozen monosaccharides bonded and is used interchangeably with "compound sugar", etc. The glycoside generally refers to an organic compound in which a saccharide is bonded to a non-saccharide substance (aglycone) (Encyclopedia MyPedia; Hitachi Solutions Create, Ltd., May 2010) and specifically refers to a compound derived from a saccharide by the substitution of a hemiacetal or hemiketal hydroxy group by an atom or a reactive group of a non-saccharide substance (Dictionary of Biochemistry, 4th edition; published by Tokyo Kagaku Dojin Co Ltd., December 2007). The glycoside according to the present invention may be a naturally occurring or artificially synthesized glycoside and includes O-glycoside as well as N-glycoside, S-glycoside, and C-glycoside.

The method for producing a fructose-added carbohydrate according to the present invention comprises a step of contacting a carbohydrate containing a terminal fructose residue and a receptor substrate with any of the following members A) to C):

A) *E. coli* expressing the following nucleic acids (a) and (b) as one polypeptide:

(a) a nucleic acid encoding an amino acid sequence having 45% or higher identity (hereinafter, also referred to as a "predetermined amino acid sequence") to an amino acid sequence of PgsA protein represented by SEQ ID NO: 6 or an amino acid sequence of CapA protein represented by SEQ ID NO: 34, and (b) a nucleic acid encoding an amino acid sequence of a β-fructofuranosidase;

B) a composition comprising dead cells of the *E. coli* expressing the nucleic acids (a) and (b) as one polypeptide; and C) a polypeptide obtained from the *E. coli* expressing the nucleic acids (a) and (b) as one polypeptide, and comprising an amino acid sequence encoded by the nucleic acid (b).

In this context, one embodiment of the "*E. coli* expressing the nucleic acids (a) and (b) as one polypeptide" of A) is schematically shown in FIG. 1. The present inventors believe, as shown in FIG. 1, that in one embodiment of the *E. coli* expressing the nucleic acids (a) and (b) as one polypeptide, a protein comprising the predetermined amino acid sequence encoded by the nucleic acid (a) is bound with the cell membrane of the *E. coli* so that the β-fructofuranosidase encoded by the nucleic acid (b) is expressed on the cell surface of the *E. coli*.

In the present invention, the "nucleic acid" refers to a compound comprising a plurality of nucleotides bonded through phosphodiester bonds and may be a deoxyribonucleic acid (DNA) or may be a ribonucleic acid (RNA). In the present invention, the "polypeptide" refers to a compound comprising a plurality of amino acids bonded through peptide bonds and is not limited by its sequence length. The polypeptide may be used interchangeably with a protein.

In the present invention, the phrase "express nucleic acids (a) and (b) as one polypeptide" means that the amino acid sequence encoded by the nucleic acid (a) and the amino acid sequence encoded by the nucleic acid (b) are expressed as one polypeptide chain. In this context, the order of the amino acid sequence encoded by the nucleic acid (a) and the amino acid sequence encoded by the nucleic acid (b) in the one polypeptide chain is not limited, and either of them may be located on the amino terminal side or on the carboxyl terminal side. The one polypeptide chain may consist only of the amino acid sequence encoded by the nucleic acid (a) and the amino acid sequence encoded by the nucleic acid (b), or one or several additional amino acids may be inserted or added to between the amino acid sequence encoded by the nucleic acid (a) and the amino acid sequence encoded by the nucleic acid (b) or to the amino terminus and/or the carboxyl terminus of these amino acid sequences.

The "amino acid sequence having 45% or higher identity (predetermined amino acid sequence) to the amino acid sequence of PgsA protein represented by SEQ ID NO: 6 or the amino acid sequence of CapA protein represented by SEQ ID NO: 34" of (a) is the amino acid sequence of an anchor protein for expression of the β-fructofuranosidase comprising the amino acid sequence encoded by the nucleic acid (b) on the cell surface of *E. coli* (hereinafter, also simply referred to as an "anchor protein"). In this context, the "PgsA protein shown in SEQ ID NO: 6" is an anchor protein derived from *Bacillus subtilis*, and the "CapA protein shown in SEQ ID NO: 34" is an anchor protein derived from a *Bacillus megaterium* DSM319 strain. In the present invention, as shown in Example 4 mentioned later, a protein comprising the predetermined amino acid sequence can be used as an anchor protein for expression of the β-fructofuranosidase on the cell surface of *E. coli*.

In the present invention, the identity of the predetermined amino acid sequence to the other amino acid sequence(s) can be confirmed according to a routine method and can be confirmed, for example, using a program such as FASTA, Basic local alignment search tool (BLAST), or Position-Specific Iterated BLAST (PSI-BLAST). In this context, the "identity" refers to the degree of exact match.

The predetermined amino acid sequence can be obtained by deleting, substituting, inserting, or adding one or several amino acids in the amino acid sequence of SEQ ID NO: 6 or SEQ ID NO: 34 such that the identity to the amino acid sequence of SEQ ID NO: 6 or SEQ ID NO: 34 does not fall within a range lower than 45%. Also, the predetermined amino acid sequence can be obtained by homology search for the amino acid sequence of SEQ ID NO: 6 or SEQ ID NO: 34 according to a routine method from an amino acid sequence database such as Protein Information Resource (PIR), SWISS-PROT, TrEMBL, Protein Research Foundation (PRF), or GenPept (NCBI Protein database) using a program such as FASTA, Basic local alignment search tool (BLAST), or Position-Specific Iterated BLAST (PSI-BLAST).

In this context, in the present invention, examples of the number of amino acids to be deleted, substituted, inserted, or added in the phrase "deleting, substituting, inserting, or adding one or several amino acids in the amino acid sequence of SEQ ID NO: 6 or SEQ ID NO: 34 such that the identity to the amino acid sequence of SEQ ID NO: 6 or SEQ ID NO: 34 does not fall within a range lower than 45%" can include 1 to 200, 1 to 180, 1 to 160, 1 to 140, 1 to 120, 1 to 100, and 1 to 80, preferably 1 to 60, more preferably 1 to 50, further preferably 1 to 40, still further preferably 1 to 30.

The predetermined amino acid sequence may be derived from any organism including bacteria, yeasts, molds, and plants. Among such predetermined amino acid sequences, examples of the amino acid sequence having 45% or higher identity to the amino acid sequence of PgsA protein represented by SEQ ID NO: 6 can include an amino acid sequence of an anchor protein derived from *Bacillus tequilensis* (National Center for Biotechnology Information (NCBI) WP_024714260.1; identity: 96%), an amino acid sequence of an anchor protein derived from *Bacillus atrophaeus* (NCBI WP_03326671.1; identity: 86%), an amino acid sequence of an anchor protein derived from *Bacillus siamensis* (NCBI WP_016937733.1; identity: 78%), and an amino acid sequence of an anchor protein derived from *Bacillus sonorensis* (NCBI WP_006639316.1; identity: 66%).

Among such predetermined amino acid sequences, examples of the amino acid sequence having 45% or higher identity to the amino acid sequence of CapA protein represented by SEQ ID NO: 34 can include an amino acid sequence of an anchor protein derived from *Bacillus flexus* (NCBI WP_025908233.1; identity: 73%), an amino acid sequence of an anchor protein derived from *Bacillus anthracis* (NCBI WP_001253153.1; identity: 53%), an amino acid sequence of an anchor protein derived from *Bacillus cereus* (NCBI WP_001996162.1; identity: 53%), an amino acid sequence of an anchor protein derived from *Bacillus endophyticus* (NCBI WP_019393395.1; identity: 52%), an amino acid sequence of an anchor protein derived from *Bacillus thuringiensis* (NCBI WP_001170049.1; identity: 51%), an amino acid sequence of an anchor protein derived from *Bacillus megaterium* (NCBI WP_013082091.1; identity: 51%), an amino acid sequence of an anchor protein derived from *Bacillus licheniformis* (NCBI AGS77947.1; identity: 47%), an amino acid sequence of an anchor protein derived from *Bacillus safensis* (NCBI WP_024423669.1; identity: 47%), an amino acid sequence of an anchor protein derived from *Bacillus pumilus* (NCBI WP_017360004.1; identity: 47%), an amino acid sequence of an anchor protein derived from *Bacillus stratosphericus* (NCBI WP_007497516.1; identity: 47%), an amino acid sequence of an anchor protein derived from *Bacillus siamensis* (NCBI WP_016937733.1; identity: 47%), an amino acid sequence of an anchor protein derived from *Bacillus vallismortis* (NCBI WP_010328824.1; identity: 46%), and an amino acid sequence of an anchor protein derived from *Bacillus mojavensis* (NCBI WP_010332115.1; identity: 46%).

The "β-fructofuranosidase" according to the present invention is an enzyme that recognizes fructose in a carbohydrate containing a terminal fructose residue and has the activity of hydrolyzing the bond at the fructose residue (fructose hydrolysis activity) and the activity of transferring fructose resulting from the hydrolysis to a receptor substrate (fructose transfer activity). The "β-fructofuranosidase" according to the present invention may be a wild-type β-fructofuranosidase derived from an organism such as a yeast, a mold, or a plant or may be a β-fructofuranosidase comprising an amino acid sequence derived from the amino acid sequence of the wild-type β-fructofuranosidase by the introduction of one or two or more amino acid mutations. In the present invention, the "β-fructofuranosidase" may be used interchangeably with "fructosyltransferase", "saccharase", "β-D-fructofuranosidase", "invertase", or "invertin".

In this context, in the present invention, the "receptor substrate" refers to a substance capable of receiving fructose in response to the transfer of the fructose by the fructose transfer activity of the β-fructofuranosidase. The "donor substrate" refers to a substance capable of donating fructose to the receptor substrate in response to the hydrolysis of the bond at the fructose residue by the fructose hydrolysis activity of the β-fructofuranosidase.

Specifically, in the present invention, the "carbohydrate containing a terminal fructose residue" refers to the donor substrate. Specific examples of the "carbohydrate containing a terminal fructose residue" according to the present invention can include: disaccharides containing a terminal fructose residue, such as sucrose; oligosaccharides containing a terminal fructose residue, such as kestose; polysaccharides containing a terminal fructose residue; sugar alcohols containing a terminal fructose residue; and glycosides containing a terminal fructose residue.

The "receptor substrate" according to the present invention may be a carbohydrate such as a monosaccharide, a disaccharide, an oligosaccharide, or a glycoside, or may be a non-carbohydrate substance such as hydroquinone, as shown in Examples 6(1) and 6(2) mentioned later. The method for producing a fructose-added carbohydrate according to the present invention can produce a disaccharide, for example, by using a monosaccharide as the receptor substrate, can produce an oligosaccharide by using a disaccharide or an oligosaccharide as the receptor substrate, and can produce a glycoside by using a non-saccharide substance as the receptor substrate.

In the method for producing a fructose-added carbohydrate according to the present invention, the "carbohydrate containing a terminal fructose residue" and the "receptor substrate" may be the same substances or may be different substances.

Specific examples of the "amino acid sequence of a β-fructofuranosidase" according to the present invention can include an amino acid sequence of a β-fructofuranosidase derived from *Beijerinckia indica* subsp. *Indica* NBRC3744 (SEQ ID NO: 2), an amino acid sequence of a β-fructofuranosidase derived from *Burkholderia phymatum* STM815 (GenBank: ACC75109.1; SEQ ID NO: 18), and an amino acid sequence of a β-fructofuranosidase derived from *Aspergillus kawachii* IFO4303 (GenBank: GAA88101.1; SEQ ID NO: 22).

In the present invention, the nucleic acid (a) or (b) encoding the predetermined amino acid sequence or the amino acid sequence of a β-fructofuranosidase (hereinafter, collectively referred to as an "amino acid sequence according to the present invention") can be obtained by polymerase chain reaction (PCR) using, as a template, a nucleic acid extracted from an organism expressing a protein consisting of the amino acid sequence according to the present invention. Alternatively, the sequence of the nucleic acid is identified according to a known genetic code indicating the correspondence between codons and amino acids on the basis of the amino acid sequence according to the present invention, and then, the nucleic acid can also be synthesized using any of various commercially available nucleic acid synthesizers.

The "*E. coli* (*Escherichia coli*)" according to the present invention may be any strain as long as the strain can express the nucleic acids (a) and (b) as one polypeptide.

The "*E. coli* expressing the nucleic acids (a) and (b) as one polypeptide" according to the present invention can be obtained by transferring a nucleic acid designed to express the nucleic acids (a) and (b) as one polypeptide to *E. coli* according to a routine method. Examples of such a method can include methods shown in Examples 1(2) and 1(5) mentioned later. Specifically, first, the nucleic acids (a) and (b) are inserted to between a promoter sequence and a terminator sequence in one vector to obtain a recombinant vector. In this respect, *E. coli* harboring the recombinant vector can express the nucleic acids (a) and (b) as one polypeptide unless a stop codon is positioned between the nucleic acid (a) and the nucleic acid (b). Subsequently, the obtained recombinant vector is transferred to *E. coli*, which can then be cultured for a given period to obtain *E. coli* expressing the nucleic acids (a) and (b) as one polypeptide.

Next, the "composition comprising dead cells of the *E. coli* expressing the nucleic acids (a) and (b) as one polypeptide" of B) according to the present invention is not limited by its form as long as the composition comprises dead cells of the *E. coli* expressing the nucleic acids (a) and (b) as one polypeptide. The composition may be, for example, in a powder form or in a liquid form. The composition B) can be obtained, for example, by lysing, disinfecting, or sterilizing the aforementioned *E. coli* expressing the nucleic acids (a) and (b) as one polypeptide according to the present invention. In this context, examples of the method for lysing, disinfecting, or sterilizing the *E. coli* can include a lysis method, a disinfection method, or a sterilization method generally used for bacteria and can specifically include a method which involves suspending the *E. coli* in a hypertonic solution, and a method which involves subjecting the *E. coli* to homogenization, grinding, freezing-thawing, ultrasonication, or heat treatment. The composition B) may or may not be subjected to some treatment such as salt precipitation, solvent precipitation, dialysis, ultrafiltration, gel filtration, SDS-polyacrylamide gel electrophoresis, ion-exchange chromatography, affinity chromatography, hydrophobic chromatography, reverse-phase chromatography, or isoelectric focusing electrophoresis as long as the resulting composition comprises a component corresponding to the dead cells of the *E. coli* expressing the nucleic acids (a) and (b) as one polypeptide.

Next, the "polypeptide obtained from the *E. coli* expressing the nucleic acids (a) and (b) as one polypeptide, and comprising an amino acid sequence encoded by the nucleic acid (b)" of C) according to the present invention may be a polypeptide consisting only of the amino acid sequence encoded by the nucleic acid (b) or may be a polypeptide comprising an amino acid sequence derived from the amino acid sequence encoded by the nucleic acid (b) by the addition of one or several amino acids to the amino terminus and/or the carboxyl terminus thereof as long as the polypeptide is a polypeptide obtained from the *E. coli* expressing the nucleic acids (a) and (b) as one polypeptide and comprises the amino acid sequence encoded by the nucleic acid (b).

The polypeptide C) can be obtained, for example, by extracting or purifying the polypeptide from the *E. coli* expressing the nucleic acids (a) and (b) as one polypeptide according to a routine method. Examples of the method for extracting or purifying the polypeptide can include methods such as homogenization, grinding, suspension in a buffer solution, freezing-thawing, ultrasonication, centrifugation, heat treatment, salt precipitation, solvent precipitation, dialysis, ultrafiltration, gel filtration, SDS-polyacrylamide gel electrophoresis, ion-exchange chromatography, affinity chromatography, hydrophobic chromatography, reverse-phase chromatography, or isoelectric focusing electrophoresis. More conveniently, the *E. coli* expressing the nucleic acids (a) and (b) as one polypeptide may be obtained directly as the polypeptide C) according to the present invention. Specifically, the polypeptide C) may be in a cell membrane-bound state of the *E. coli* expressing the nucleic acids (a) and (b) as one polypeptide or may be in a cell membrane-unbound state of this *E. coli*.

In the method for producing a fructose-added carbohydrate according to the present invention, examples of the method for contacting the carbohydrate containing a terminal fructose residue and the receptor substrate with any of the members A) to C) can include a method which involves adding any of the members A) to C) to a solution containing the carbohydrate containing a terminal fructose residue and the receptor substrate and leaving the mixture standing or shaking the mixture at 20° C. to 60° C. for a given time.

The method for producing a fructose-added carbohydrate according to the present invention may have an additional step without impairing the features of the present invention, and may have, for example, a step of separating the fructose-added carbohydrate by chromatography, a crystallization step such as boiling down crystallization, a drying step, a washing step, a filtration step, a disinfection step, and a step of adding a food additive.

The present invention also provides E. coli. The E. coli according to the present invention is E. coli expressible of or expressing the following nucleic acids (a) and (b) as one polypeptide: (a) a nucleic acid encoding an amino acid sequence having 45% or higher identity (predetermined amino acid sequence) to the amino acid sequence of PgsA protein represented by SEQ ID NO: 6 or the amino acid sequence of CapA protein represented by SEQ ID NO: 34, and (b) a nucleic acid encoding an amino acid sequence of a β-fructofuranosidase.

The description about the same or equivalent constitution of the E. coli according to the present invention as in the aforementioned method for producing a fructose-added carbohydrate according to the present invention will be omitted here.

In this context, the "E. coli expressible of the nucleic acids (a) and (b) as one polypeptide" refers to E. coli that comprises the nucleic acids (a) and (b) in a form where the nucleic acids can be expressed as one polypeptide, but has not yet expressed the nucleic acids (a) and (b) as one polypeptide.

The "E. coli expressible of the nucleic acids (a) and (b) as one polypeptide" according to the present invention can be obtained in the same way as the aforementioned method for obtaining the "E. coli expressing the nucleic acids (a) and (b) as one polypeptide" according to the present invention by using an expression inducible promoter sequence, which requires some induction factor for the initiation of transcription, or an operator sequence, which requires the dissociation of a repressor for the initiation of transcription.

Specifically, in the case of using an expression inducible promoter sequence, the "E. coli expressible of the nucleic acids (a) and (b) as one polypeptide" can be obtained by culture in the absence of an induction factor. Examples of such an expression inducible promoter sequence can include a promoter sequence of alcohol dehydrogenase gene (induction factor: alcohol; Waring R B et al., Gene, Vol. 79, p. 119-130, 1989), a promoter sequence of α-amylase gene (induction factor: starch, maltose, etc.; Tada S. et al., Mol. Gen. Genet., Vol. 229, p. 301-306, 1991), and a promoter sequence, such as ThiA, derived from a bacterium of the genus Aspergillus (induction factor: thiamine; Shoji J Y et al., FEMS Microbiol. Lett., Vol. 244, p. 41-46, 2005).

In the case of using an operator sequence, which requires the dissociation of a repressor, the "E. coli expressible of the nucleic acids (a) and (b) as one polypeptide" can be obtained by culture in the absence of a factor necessary for the dissociation of a repressor. Examples of such an operator sequence can include lac operator sequence (factor necessary for the dissociation of a repressor: lactose or isopropyl-β-D-thiogalactopyranoside (IPTG)).

The present invention further provides a composition. The composition according to the present invention is a composition comprising dead cells of the E. coli expressing the nucleic acids (a) and (b) as one polypeptide. The present invention also provides a polypeptide. The polypeptide according to the present invention is a polypeptide obtained from the E. coli expressing the nucleic acids (a) and (b) as one polypeptide, and comprising an amino acid sequence encoded by the nucleic acid (b). The description about the same or equivalent constitution of the composition and the polypeptide according to the present invention as in the aforementioned method for producing a fructose-added carbohydrate according to the present invention will be omitted here.

Hereinafter, the present invention will be described with reference to each Example. The technical scope of the present invention is not intended to be limited by the features indicated by these Examples.

EXAMPLES

<Example 1> Construction of β-fructofuranosidase Expression System (1) Obtainment of Nucleic Acid Encoding Amino Acid Sequence of β-fructofuranosidase A gene of a β-fructofuranosidase of *Beijerinckia indica* subsp. *indica* NBRC3744 (hereinafter, abbreviated to "*B. Indica*") was cloned. Specifically, the genomic DNA of *B. Indica* was first extracted according to a routine method. Subsequently, DNA encoding the amino acid sequence of the *B. Indica*-derived β-fructofuranosidase was amplified by polymerase chain reaction (PCR) under conditions given below using primers of SEQ ID NO: 3 and SEQ ID NO: 4 given below. The full-length nucleotide sequence was determined by sequencing according to a routine method. The full-length nucleotide sequence of the DNA encoding the amino acid sequence of the *B. Indica*-derived β-fructofuranosidase is shown in SEQ ID NO: 1, and the amino acid sequence of the *B. Indica*-derived β-fructofuranosidase encoded thereby is shown in SEQ ID NO: 2.

<<PCR Conditions for Amplification of DNA Encoding Amino Acid Sequence of *B. Indica*-Derived β-fructofuranosidase>>

Template: genomic DNA of *B. Indica*
Forward primer: 5'-ATGGCAAGTCGATCGTTTAAT-GTTTGTATAC-3' (SEQ ID NO: 3)
Reverse primer: 5'-TTTACCAGACTCGAGTTACTGGC-CGTTCGTGAC-3' (SEQ ID NO: 4)
Enzyme for PCR: KOD-Plus- (Toyobo Co., Ltd.)
Reaction conditions: 30 cycles each involving 95° C. for 10 seconds, 60° C. for 20 seconds, and 68° C. for 2 minutes Subsequently, a signal sequence of the β-fructofuranosidase was predicted using the SignalP 4.1 server. The signal sequence corresponds to positions 1 to 28 in SEQ ID NO: 2.

(2) Preparation of Recombinant Vector of Cell Surface Expression System

DNA encoding *Bacillus subtilis* PgsA protein (GenBank: AB016245.1) was amplified by PCR under conditions given below. The obtained PCR product was digested with restriction enzymes NdeI and BglII according to a routine method. This fragment was designated as DNA fragment 1. Also, the PCR product was sequenced according to a routine method to confirm the nucleotide sequence of the DNA encoding the PgsA protein. The nucleotide sequence of the DNA encoding the PgsA protein is shown in SEQ ID NO: 5, and the amino acid sequence of the PgsA protein encoded thereby is shown in SEQ ID NO: 6.

<<PCR Conditions for Amplification of DNA Encoding PgsA Protein>>

Template: genomic DNA of *Bacillus subtilis* (IAM1026, ATCC9466)

Forward primer (NdeI site is underlined): 5'-AAACATAT-GAAAAAAGAACTGAGCTTTCATG-3' (SEQ ID NO: 7)
Reverse primer (BglII site is underlined): 5'-AAAAGATCTTTTAGATTTTAGTTTGTCACTATG-3' (SEQ ID NO: 8)

Enzyme for PCR: KOD-Plus- (Toyobo Co., Ltd.)
Reaction conditions: 30 cycles each involving 95° C. for 10 seconds, 60° C. for 20 seconds, and 68° C. for 2 minutes Next, the DNA encoding the amino acid sequence of the *B. Indica*-derived β-fructofuranosidase was amplified by PCR under conditions given below, and the PCR product was digested with restriction enzymes BamHI and XhoI according to a routine method. This fragment was designated as DNA fragment 2.

<<PCR Conditions for Amplification of DNA Encoding Amino Acid Sequence of *B. Indica*-Derived β-fructofuranosidase>>

Template: genomic DNA of *B. Indica* of this Example 1(1)

```
Forward primer (BamHI site is underlined):
                                         (SEQ ID NO: 9)
5'-AAAGGATCCTCGGGTTACCCGATACCGACTCCGCATTCGGGACA-3'

Reverse primer (XhoI site is underlined):
                                         (SEQ ID NO: 10)
5'-CCCCTCGAGTTACTGGCCGTTCGTGACACCATGGCCATTAAC-3'
```

Enzyme for PCR: KOD-Plus- (Toyobo Co., Ltd.)
Reaction conditions: 20 cycles each involving 95° C. for 10 seconds, 60° C. for 20 seconds, and 68° C. for 2 minutes Subsequently, DNA fragment 1 and DNA fragment 2 were inserted to the NdeI site and the XhoI site of a pCDFDuet-1 plasmid (Merck KGaA) using DNA Ligation Kit Ver. 2.1 (Takara Bio Inc.) according to the attached instruction manual. The resulting vector was designated as a pCDF-pgsA-*indica* recombinant vector.

The pCDF-pgsA-*indica* recombinant vector was digested with restriction enzymes NdeI and XhoI according to a routine method, then electrophoresed, and purified to obtain DNA encoding the amino acid sequences of the PgsA protein and the *B. Indica*-derived β-fructofuranosidase so as to be expressible as one polypeptide. This fragment was designated as DNA fragment 3. Subsequently, DNA fragment 3 was inserted to a pET42a(+) plasmid (Merck KGaA) similarly digested with NdeI and XhoI using Ligation high Ver. 2 (Toyobo Co., Ltd.). The resulting vector was designated as a pET-pgsA-*indica* recombinant vector.

(3) Preparation of Recombinant Vector of Intracellular Expression System

DNA containing no DNA encoding the pgsA protein was amplified by PCR under conditions given below using the pCDF-pgsA-*indica* recombinant vector of this Example 1(2) as a template. This amplified fragment was designated as DNA fragment 4. Subsequently, DNA fragment 4 was self-ligated using Ligation high Ver. 2 (Toyobo Co., Ltd.). The resulting vector was designated as a pCDF-*indica* recombinant vector.

<<PCR Conditions for Amplification of pCDFDuet-1 Plasmid-Derived DNA Having Insert of DNA Encoding Amino Acid Sequence of *B. Indica*-Derived β-fructofuranosidase>>

Template: pCDF-pgsA-*indica* recombinant vector of this Example 1(2)

```
                                         (SEQ ID NO: 11)
Forward primer: 5'-CATATGTCGGGTTACCCGATACCGAC-3'

(SEQ ID NO: 12)
Reverse primer: 5'-TATATCTCCTTCTTATACTTAACTAATA-3'
```

Enzyme for PCR: KOD-Plus-Neo (Toyobo Co., Ltd.)
Reaction conditions: 25 cycles each involving 98° C. for 10 seconds, 59° C. for 30 seconds, and 68° C. for 2 minutes and 40 seconds The pCDF-*indica* recombinant vector was digested with restriction enzymes NdeI and XhoI according to a routine method to obtain DNA encoding the amino acid sequence of the *B. Indica*-derived β-fructofuranosidase. This fragment was designated as DNA fragment 5. Subsequently, DNA fragment 5 was inserted to a pET42a(+) plasmid (Merck KGaA) similarly digested with NdeI and XhoI using Ligation high Ver. 2 (Toyobo Co., Ltd.). The resulting vector was designated as a pET-*indica* recombinant vector.

(4) Preparation of Recombinant Vector of Intracellular Expression System (Soluble)

The DNA encoding the amino acid sequence of the *B. Indica*-derived β-fructofuranosidase was amplified by PCR under conditions given below. This amplified fragment was designated as DNA fragment 6.

<<PCR Conditions for Amplification of DNA Encoding Amino Acid Sequence of *B. Indica*-Derived β-fructofuranosidase>>

Template: pCDF-*indica* recombinant vector of this Example 1(3)

```
Forward primer:
                                         (SEQ ID NO: 13)
5'-GATGGTTCAACTAGTTCGGGTTACCCGATACCG-3'

Reverse primer:
                                         (SEQ ID NO: 14)
5'-GTGGTGGTGCTCGAGTTACTGGCCGTTCGTGA-3'
```

Enzyme for PCR: KOD-Plus-Neo (Toyobo Co., Ltd.)
Reaction conditions: 25 cycles each involving 98° C. for 10 seconds and 68° C. for 50 seconds Also, pET42a(+) plasmid-derived DNA was amplified by PCR under conditions given below. This amplified fragment was designated as DNA fragment 7.

<<PCR Conditions for Amplification of pET42a(+) Plasmid-Derived DNA>>

Template: pET42a(+) plasmid (Merck KGaA)

```
Forward primer:
                                         (SEQ ID NO: 15)
5'-CTCGAGCACCACCACCACCACCACCACTAATT-3'

(SEQ ID NO: 16)
Reverse primer: 5'-ACTAGTTGAACCATCCGATTT-3'
```

Enzyme for PCR: KOD-Plus-Neo (Toyobo Co., Ltd.)
Reaction conditions: 25 cycles each involving 98° C. for 10 seconds and 68° C. for 2 minutes and 50 seconds Subsequently, DNA fragment 6 and DNA fragment 7 were ligated using In-Fusion HD Cloning Kit (Takara Bio Inc.) such that the *B. Indica*-derived β-fructofuranosidase and glutathione-S-transferase (GST) contained in the pET42a(+) plasmid were expressed as one polypeptide. The resulting vector was designated as a pET-GST-*indica* recombinant vector. GST is a soluble protein and reportedly improves the solubility of a protein of interest by expression of GST and the protein of interest as a fusion protein.

(5) Transformation and Culture of Transformant

The pCDF-pgsA-*indica* recombinant vector and the pET-pgsA-*indica* recombinant vector of this Example 1(2), the pCDF-*indica* recombinant vector and the pET-*indica* recombinant vector of this Example 1(3), and the pET-GST-*indica* recombinant vector of this Example 1(4) were each transferred to competent cells (Cosmo Bio Co., Ltd.) of an *E. coli* BL21 (DE3) strain to obtain recombinant *E. coli* as a transformant.

Each transformant was plate-cultured overnight at 37° C. Then, clones of the recombinant *E. coli* were picked up, inoculated to 1 mL of M9 SEED medium, and shake-cultured at 220 rpm at 30° C. for 20 hours. Subsequently, a 10 μL aliquot of the culture solution was inoculated to 2 mL of M9 Main medium and shake-cultured at 220 rpm at 25° C. for 24 hours. The composition of the M9 SEED medium and the M9 Main medium is shown below. The antibiotics used in the M9 SEED medium and the M9 Main medium were streptomycin (final concentration: 50 μg/mL) for the *E. coli* transformed with the pCDF-pgsA-*indica* recombinant vector or the pCDF-*indica* recombinant vector, and kanamycin (final concentration: 30 μg/mL) for the *E. coli* transformed with the pET-pgsA-*indica* recombinant vector, the pET-*indica* recombinant vector, or the pET-GST-*indica* recombinant vector.

M9 SEED medium (a total of 100 mL): 72 mL of water, 20 mL of 5×M9 salt, 5 mL of 20% casamino acid, 2 mL of 20% D-glucose, 1 mL of 2 mg/mL thymine, 0.2 mL of 50 mM $CaCl_2$, 40 μL of 2.5 M $MgCl_2$, 28 μL of 100 mg/mL $FeSO_4$, and the corresponding antibiotic M9 Main medium (a total of 100 mL): 67 mL of water, 20 mL of 5×M9 salt, 5 mL of 20% casamino acid, 1 mL of 2 mg/mL thymine, 0.2 mL of 50 mM $CaCl_2$, 28 μL of 100 mg/mL $FeSO_4$, 2 mL of Overnight Express Autoinduction System 1 (O.N.E.; Merck KGaA) Sol. 1, 5 mL of O.N.E. Sol. 2, 100 μL of O.N.E. Sol. 3, and the corresponding antibiotic <Example 2> Study on Effect of Cell Surface Expression System (1) Enzymatic Reaction 2 mL of the culture solution of each recombinant *E. coli* of Example 1(5) was prepared. Then, the recombinant *E. coli* was recovered by the centrifugation of the culture solution at 12000 rpm at 4° C. for 5 minutes, and the wet weight of the bacterial cells was measured. Also, a 0.04 M sodium phosphate buffer (pH 7.0) containing 30 (w/w) % sucrose was prepared and used as a 30% sucrose solution. 2 mL of the culture solution of the recombinant *E. coli* was suspended by the addition of 350 μL of the 30% sucrose solution. This suspension was shaken at 200 rpm at 30° C. for 3 hours for the enzymatic reaction of the β-fructofuranosidase to prepare reaction solutions. Upon contact with a solution having a solute concentration of approximately 30 (w/w) %, *E. coli* is lysed by water efflux from the bacterial cells through osmotic pressure.

(2) Confirmation of Saccharide Composition

50 μL of each reaction solution of this Example 2(1) was diluted by the addition of 950 μL of water and then heated at 100° C. for 10 minutes. Subsequently, a supernatant was recovered by centrifugation at 15000×g at 4° C. for 10 minutes and filtered through a filter having a pore size of 0.45 μm, and the obtained filtrate was used as an HPLC sample. Next, the HPLC sample was subjected to HPLC under conditions given below to confirm the proportion of each saccharide (monosaccharide: fructose and glucose, disaccharide: sucrose, trisaccharide or higher oligosaccharides; kestose, nystose, etc.) contained in the reaction solution. The proportion of each saccharide was calculated in percentage as a ratio of the area of each peak to the total area of all peaks detected.

<<HPLC Conditions>>

Column: two columns of SHODEX SUGAR KS_802 (8.0ϕ× 300 mm)
Mobile phase: water
Flow rate: 1.0 mL/min
Injection volume: 20 μL
Temperature: 50° C.
Detection: differential refractive index detector (RID; Showa Denko K.K.)

Next, the mass of the sucrose (118.65 mg; mass of the sucrose contained in 350 μL of the sucrose solution) used in the enzymatic reaction was multiplied by the area % of the trisaccharide or higher oligosaccharides to calculate the amount of the trisaccharide or higher oligosaccharides. This amount was used as the amount of oligosaccharides formed. The amount of oligosaccharides formed was divided by the bacterial cell weight to calculate the amount of oligosaccharides formed in percentage per bacterial cell weight. This amount was used as the rate of formation of oligosaccharides. The mass (118.65 mg) of the sucrose used in the enzymatic reaction was multiplied by a value obtained by subtracting the area % of the sucrose from 100% to calculate the amount of sucrose consumed. The amount of sucrose consumed was divided by the bacterial cell weight to calculate the amount of sucrose consumed in percentage per bacterial cell weight. This amount was used as the rate of consumption of sucrose. The results are shown in Table 1.

TABLE 1

| Expression manner of β-fructofuranosidase | Recombinant vector | Bacterial cell weight | Amount of oligosaccharides formed (mg) | Amount of sucrose consumed (mg) | Rate of formation of oligosaccharides (%) (Amount of oligosaccharides formed/ Bacterial cell weight) × 100 | Rate of consumption of sucrose (%) (Amount of sucrose consumed/ Bacterial cell weight) × 100 |
|---|---|---|---|---|---|---|
| Intracellular expression | pCDF-indica | 60.4 | 7.2 | 18.7 | 11.9 | 30.9 |
| Cell surface expression | pCDF-pgsA-indica | 38.6 | 30.3 | 104.2 | 78.6 | 269.9 |
| Intracellular expression | pET-indica | 45.7 | 12.4 | 34.4 | 27.1 | 75.3 |
| Intracellular expression (soluble) | pET-GST-indica | 41.0 | 4.6 | 18.1 | 11.3 | 44.2 |
| Cell surface expression | pET-pgsA-indica | 22.5 | 26.2 | 82.5 | 116.4 | 366.6 |

As shown in Table 1, the rate of formation of oligosaccharides was 11.9% in the reaction solution of the *E. coli* transformed with the pCDF-*indica* recombinant vector whereas the rate of formation of oligosaccharides was 78.6% in the reaction solution of the *E. coli* transformed with the pCDF-pgsA-*indica* recombinant vector and was at least 6.6 times larger. The rate of formation of oligosaccharides was 27.1% and 11.3% in the reaction solutions of the E. coif transformed with the pET-*indica* recombinant vector and the pET-GST-*indica* recombinant vector, respectively, whereas the rate of formation of oligosaccharides was 116.4% in the reaction solution of the *E. coli* transformed with the pET-pgsA-*indica* recombinant vector and was at least 4.2 times and 10.3 times larger, respectively.

In both cases of using the recombinant vector derived from the pCDFDuet-1 plasmid and using the recombinant vector derived from the pET42a(+) plasmid, the expression of the β-fructofuranosidase on the cell surface of *E. coli* was found to remarkably enhance the efficiency of oligosaccharide formation as compared with the intracellular expression of the β-fructofuranosidase or the intracellular expression thereof as a soluble protein. These results demonstrated that a fructose-added carbohydrate can be produced very efficiently by expressing an anchor protein for expression on the cell surface and a β-fructofuranosidase as one polypeptide, irrespective of the type of a vector for use in transformation.

<Example 3> Study on Origin of β-fructofuranosidase

The effect of being able to efficiently produce a fructose-added carbohydrate by expressing an anchor protein for expression on the cell surface, and a β-fructofuranosidase as one polypeptide was studied for whether or not to be exerted irrespective of the origin of the β-fructofuranosidase. Specifically, a *Burkholderia phymatum* STM815 (hereinafter, abbreviated to "Burk") β-fructofuranosidase belonging to the same family 68 as that of the *B. Indica*-derived β-fructofuranosidase and an *Aspergillus kawachii* IFO4303 (hereinafter, abbreviated to "*Kawachii*") β-fructofuranosidase belonging to family 32 were examined.

(1) Obtainment of Nucleic Acid Encoding Amino Acid Sequence of β-Fructofuranosidase
[1-1] Burk-Derived β-fructofuranosidase A gene of the Burk β-fructofuranosidase was cloned and sequenced by the method described in Example 1(1). However, the PCR conditions were as described below. The full-length nucleotide sequence of the DNA encoding the amino acid sequence of the Burk-derived β-fructofuranosidase is shown in SEQ ID NO: 17, and the amino acid sequence of the Burk-derived β-fructofuranosidase encoded thereby is shown in SEQ ID NO: 18. A signal sequence corresponds to positions 1 to 35 in SEQ ID NO: 18. The DNA encoding the amino acid sequence of the Burk-derived β-fructofuranosidase was amplified by PCR under conditions given below and designated as DNA fragment 8.
<<PCR Conditions for Amplification of DNA Encoding Amino Acid Sequence of Burk-Derived β-fructofuranosidase>>
Template: genomic DNA of Burk Forward primer:
(SEQ ID NO: 19)
5'-AAACTAAAATCTAAAAGATCTCAGACTGCAACGCCAGGCTTCCCCG-3'

Reverse primer:
(SEQ ID NO: 20)
5'-GGTTTCTTTACCAGACTCGAGTTACTGGCTGTTGCCGCCCTGCCCGTTTCC-3'

Enzyme for PCR: KOD-Plus- (Toyobo Co., Ltd.)
Reaction conditions: 21 cycles each involving 94° C. for 15 seconds, 58° C. for 20 seconds, and 68° C. for 2 minutes
[1-2] *Kawachii*-Derived β-fructofuranosidase Next, DNA encoding the *Kawachii* β-fructofuranosidase (GenBank: GAA88101.1) was obtained by artificial synthesis in a request to GenScript Japan Inc. The full-length nucleotide sequence of the DNA encoding the amino acid sequence of the *Kawachii*-derived β-fructofuranosidase is shown in SEQ ID NO: 21, and the amino acid sequence of the *kawachii*-derived β-fructofuranosidase encoded thereby is shown in SEQ ID NO: 22. A signal sequence corresponds to positions 1 to 24 in SEQ ID NO: 22.

(2) Preparation of Recombinant Vector of Cell Surface Expression System
[2-1] Burk-Derived β-fructofuranosidase pCDFDuet-1 plasmid-derived DNA that had an insert of the DNA encoding the PgsA protein and contained no DNA encoding the amino acid sequence of the *B. Indica*-derived β-fructofuranosidase was amplified by PCR under conditions given below. This amplified fragment was designated as DNA fragment 9.
<<PCR Conditions for Amplification of pCDFDuet-1 Plasmid-Derived DNA Having Insert of DNA Encoding PgsA Protein>>
Template: pCDF-pgsA-*indica* recombinant vector of Example 1(2)

Forward primer:
(SEQ ID NO: 23)
5'-TCTGGTAAAGAAACCGCTGCTGCGAAATTT-3'

Reverse primer:
(SEQ ID NO: 24)
5'-TTTAGATTTTAGTTTGTCACTATGATCAAT-3'

Reaction conditions: 25 cycles each involving 98° C. for 10 seconds and 68° C. for 2 minutes and 25 seconds Subsequently, DNA fragment 8 of this Example 3(1)[1-1] and DNA fragment 9 were ligated using In-Fusion HD Cloning Kit (Takara Bio Inc.) according to the attached instruction manual. The resulting vector was designated as a pCDF-pgsA-burk recombinant vector.
[2-2] *Kawachii*-Derived β-fructofuranosidase The DNA encoding the amino acid sequence of the *Kawachii*-derived β-fructofuranosidase was amplified by PCR under conditions given below. This amplified fragment was designated as DNA fragment 10.
<<PCR Conditions for Amplification of DNA Encoding Amino Acid Sequence of *Kawachii*-Derived β-fructofuranosidase>>
Template: DNA encoding the amino acid sequence of the *Kawachii*-derived β-fructofuranosidase of this Example 3(1)[1-2]

Forward primer:
(SEQ ID NO: 25)
5'-AAATCTAAAAGATCCTCCGTGGTCATCGACTAC-3'

Reverse primer:

-continued

```
                                                   (SEQ ID NO: 26)
5'-TTTACCAGACTCGAGTCAATACTGACGATCCGGC-3'
```

Enzyme for PCR: KOD-Plus-Neo (Toyobo Co., Ltd.)
Reaction conditions: 25 cycles each involving 98° C. for 10 seconds and 68° C. for 50 seconds DNA containing no DNA encoding the amino acid sequence of the *B. Indica*-derived β-fructofuranosidase was amplified by PCR under conditions given below using the pCDF-pgsA-*indica* recombinant vector of Example 1(2) as a template. This amplified fragment was designated as DNA fragment 11.

<<PCR Conditions for Amplification of pCDFDuet-1 Plasmid-Derived DNA Having Insert of DNA Encoding PgsA Protein>>

Template: pCDF-pgsA-*indica* recombinant vector of Example 1(2)

```
Forward primer:
                                                   (SEQ ID NO: 27)
5'-CTCGAGTCTGGTAAAGAAACCGCTGCTGCGAAA-3'

Reverse primer:
                                                   (SEQ ID NO: 28)
5'-GGATCTTTTAGATTTTAGTTTGTCACTATGATCAA-3'
```

Enzyme for PCR: KOD-Plus-Neo (Toyobo Co., Ltd.)
Reaction conditions: 25 cycles each involving 98° C. for 10 seconds and 68° C. for 2 minutes and 25 seconds Subsequently, DNA fragment 10 and DNA fragment 11 were ligated using In-Fusion HD Cloning Kit (Takara Bio Inc.) according to the attached instruction manual. The resulting vector was designated as a pCDF-pgsA-*kawachii* recombinant vector.

(3) Preparation of Recombinant Vector of Intracellular Expression System

[3-1] Burk-Derived β-fructofuranosidase

DNA containing no DNA encoding the pgsA protein was amplified by PCR under conditions given below using the pCDF-pgsA-burk recombinant vector of this Example 3(2)[2-1] as a template. This amplified fragment was designated as DNA fragment 12. Subsequently, DNA fragment 12 was self-ligated using Ligation high Ver. 2 (Toyobo Co., Ltd.) according to the attached instruction manual. The resulting vector was designated as a pCDF-burk recombinant vector.

<<PCR Conditions for Amplification of pCDFDuet-1 Plasmid-Derived DNA Having Insert of DNA Encoding Amino Acid Sequence of Burk-Derived β-fructofuranosidase>>

Template: pCDF-pgsA-burk recombinant vector of this Example 3(2)[2-1]

```
                                                   (SEQ ID NO: 29)
Forward primer: 5'-CATATGCAGACTGCAACGCCAGGCT-3'

(SEQ ID NO: 30)
Reverse primer: 5'-TATATCTCCTTCTTATACTTAACTAATA-3'
```

Enzyme for PCR: KOD-Plus-Neo (Toyobo Co., Ltd.)
Reaction conditions: 25 cycles each involving 98° C. for 10 seconds, 59° C. for 30 seconds, and 68° C. for 2 minutes and 40 seconds

[3-2] *Kawachii*-Derived β-fructofuranosidase

DNA containing no DNA encoding the pgsA protein was amplified by PCR under conditions given below using the pCDF-pgsA-*kawachii* recombinant vector of this Example 3(2)[2-2] as a template. This amplified fragment was designated as DNA fragment 13. Subsequently, DNA fragment 13 was self-ligated using Ligation high Ver. 2 (Toyobo Co., Ltd.) according to the attached instruction manual. The resulting vector was designated as a pCDF-*kawachii* recombinant vector.

<<PCR Conditions for Amplification of pCDFDuet-1 Plasmid-Derived DNA Having Insert of DNA Encoding Amino Acid Sequence of *Kawachii*-Derived β-fructofuranosidase>>

Template: pCDF-pgsA-*kawachii* recombinant vector of this Example 3(2)[2-2]

```
                                                   (SEQ ID NO: 31)
Forward primer: 5'-CATATGTCCGTGGTCATCGACTAC-3'

(SEQ ID NO: 32)
Reverse primer: 5'-TATATCTCCTTCTTATACTTAACTAATA-3'
```

Enzyme for PCR: KOD-Plus-Neo (Toyobo Co., Ltd.)
Reaction conditions: 25 cycles each involving 98° C. for 10 seconds, 59° C. for 30 seconds, and 68° C. for 2 minutes and 40 seconds (4) Transformation and Culture of Transformant The pCDF-pgsA-burk recombinant vector of this Example 3(2)[2-1], the pCDF-pgsA-*kawachii* recombinant vector of this Example 3(2)[2-2], the pCDF-burk recombinant vector of this Example 3(3)[3-1], and the pCDF-*kawachii* recombinant vector of this Example 3(3)[3-2] were each transferred to *E. coli* by the method described in Example 1(5), and the obtained recombinant *E. coli* was cultured.

(5) Enzymatic Reaction and Measurement of Amount of Oligosaccharides

The enzymatic reaction of the β-fructofuranosidase was performed by the method described in Example 2(1) using the culture solution of each recombinant *E. coli* of this Example 3(4). Then, the proportion of each saccharide contained in the reaction solution was measured by the method described in Example 2(2) to calculate the amount of oligosaccharides formed, the rate of formation of oligosaccharides, the amount of sucrose consumed, and the rate of consumption of sucrose. The results are shown in Table 2. For comparison, Table 2 also shows the results about the reaction solutions of the *E. coli* transformed with the pCDF-*indica* recombinant vector and the pCDF-pgsA-*indica* recombinant vector described in Table 1.

TABLE 2

| β-FFase (Family classification) | Expression manner of β-fructofuranosidase | Recombinant vector | Bacterial cell weight | Amount of oligosaccharides formed (mg) | Amount of sucrose consumed (mg) | Rate of formation of oligosaccharides (%) (Amount of oligosaccharides formed/ Bacterial cell weight) × 100 | Rate of consumption of sucrose (%) (Amount of sucrose consumed/ Bacterial cell weight) × 100 |
|---|---|---|---|---|---|---|---|
| Indica (Family68) | Intracellular expression | pCDF-indica | 60.4 | 7.2 | 18.7 | 11.9 | 30.9 |
| Indica (Family68) | Cell surface expression | pCDF-pgsA-indica | 38.6 | 30.3 | 104.2 | 78.6 | 269.9 |
| burk (Family68) | Intracellular expression | pCDF-burk | 51.9 | 19.2 | 89.6 | 37.0 | 172.6 |
| burk (Family68) | Cell surface expression | pCDF-pgsA-burk | 16.3 | 25.5 | 92.6 | 156.7 | 568.0 |
| Kawachi (Family32) | Intracellular expression | pCDF-kawachii | 54.7 | 18.9 | 105.6 | 34.5 | 193.1 |
| Kawachi (Family32) | Cell surface expression | pCDF-pgsA-kawachii | 28.0 | 68.7 | 108.6 | 245.2 | 388.0 |

As shown in Table 2, the rate of formation of oligosaccharides was 37.0% in the reaction solution of the *E. coli* transformed with the pCDF-burk recombinant vector whereas the rate of formation of oligosaccharides was 156.7% in the reaction solution of the *E. coli* transformed with the pCDF-pgsA-burk recombinant vector and was at least 4.2 times larger. The rate of formation of oligosaccharides was 34.5% in the reaction solution of the *E. coli* transformed with the pCDF-*kawachii* recombinant vector whereas the rate of formation of oligosaccharides was 245.2% in the reaction solution of the *E. coli* transformed with the pCDF-pgsA-*kawachii* recombinant vector and was at least 7.1 times larger.

The expression of the Burk-derived β-fructofuranosidase and the *Kawachii*-derived β-fructofuranosidase on the cell surface of *E. coli* was found to remarkably enhance the efficiency of oligosaccharide formation as compared with the intracellular expression thereof, as with the *B. Indica*-derived β-fructofuranosidase. These results demonstrated that a fructose-added carbohydrate can be produced very efficiently by expressing an anchor protein for expression on the cell surface and a β-fructofuranosidase as one polypeptide in the form of a fusion protein, irrespective of the difference in origin or family of the β-fructofuranosidase.

<Example 4> Study on Anchor Protein

The effect of being able to efficiently produce a fructose-added carbohydrate by expressing an anchor protein for expression on the cell surface and a β-fructofuranosidase as one polypeptide was studied for whether or not to be exerted irrespective of the type of the anchor protein. Specifically, the following anchor proteins (i) and (ii) were extracted by search using Basic Local Alignment Search Tool (BLAST) on the basis of the amino acid sequence of the PgsA protein, and examined:
(i) CapA protein of a *Bacillus megaterium* DSM319 strain having 45% identity to the amino acid sequence of the PgsA protein, and
(ii) a protein of a *Brevibacillus brevis* NBRC100599 strain (geninfo identifier (GI) No. 226313341; hereinafter, referred to as "brev protein") having 32% identity to the amino acid sequence of the PgsA protein and 36% identity to the amino acid sequence of the CapA protein.

(1) Preparation of Recombinant Vector of Cell Surface Expression System

[1-1] Amplification of DNA Encoding CapA Protein

A *E. coli* codon-optimized nucleotide sequence of a DNA sequence encoding the CapA protein was designed and used as a capA_opti gene. The nucleotide sequence of the capA_opti gene is shown in SEQ ID NO: 33, and the amino acid sequence encoded thereby is shown in SEQ ID NO: 34. Next, the DNA of the capA_opti gene was artificially synthesized, and DNA encoding the CapA protein was amplified by PCR under conditions given below using the synthesized DNA as a template. This amplified fragment was designated as DNA fragment 14.

<<PCR Conditions for Amplification of DNA Encoding CapA Protein>>

Template: artificially synthesized DNA of capA_opti gene

```
Forward primer:
                                       (SEQ ID NO: 35)
5'-TAAGAAGGAGATATACATATGAAAGAAAAGAAACTGAACTTCCAA
G-3'

Reverse primer:
                                       (SEQ ID NO: 36)
5'-CGGGTAACCCGATTGAGATCTATTTGCCTGGGCTTCGTTCTTTTT
G-3'
```

Enzyme for PCR: KOD-Plus- (Toyobo Co., Ltd.)

Reaction conditions: 21 cycles each involving 94° C. for 15 seconds, 58° C. for 20 seconds, and 68° C. for 2 minutes

[1-2] Amplification of DNA Encoding Brev Protein

The genomic DNA of a *Brevibacillus brevis* NBRC100599 strain was extracted according to a routine method. Subsequently, DNA encoding the brev protein was amplified by PCR under conditions given below. This amplified fragment was designated as DNA fragment 15. Also, the PCR product was sequenced according to a routine method to determine the full-length nucleotide sequence of the DNA encoding the brev protein. The full-length nucleotide sequence of the DNA encoding the brev protein is shown in SEQ ID NO: 37, and the amino acid sequence of the brev protein encoded thereby is shown in SEQ ID NO: 38.

<<PCR Conditions for Amplification of DNA Encoding Brev Protein>>
Template: genomic DNA of the *Brevibacillus brevis* NBRC100599 strain

```
Forward primer:
                                  (SEQ ID NO: 39)
5'-GAAGGAGATATACATATGAACGAGAACAGATCAAG-3'

Reverse primer:
                                  (SEQ ID NO: 40)
5'-GTAACCCGAGGATCTGGGGGCAGTCTCCACCGC-3'
```

Enzyme for PCR: KOD-Plus-Neo (Toyobo Co., Ltd.)
Reaction conditions: 45 cycles each involving 98° C. for 10 seconds and 68° C. for 1 minute and 10 seconds

[1-3] Preparation of Recombinant Vector
<1-3-1> CapA Protein

DNA that contained no DNA encoding the pgsA protein but encoded the amino acid sequence of the *B. Indica*-derived β-fructofuranosidase was amplified by PCR under conditions given below using the pCDF-pgsA-*indica* recombinant vector of Example 1(2) as a template. This amplified fragment was designated as DNA fragment 16. Subsequently, DNA fragment 14 of this Example 4(1)[1-1] and DNA fragment 16 were ligated using In-Fusion HD Cloning Kit (Takara Bio Inc.) according to the attached instruction manual. The resulting vector was designated as a pCDF-capA_opti-*indica* recombinant vector.

<<PCR Conditions for Amplification of pCDFDuet-1 Plasmid-Derived DNA Having Insert of DNA Encoding Amino Acid Sequence of *B. Indica*-Derived β-fructofuranosidase>>
Template: pCDF-pgsA-*indica* recombinant vector of Example 1(2)

```
Forward primer:
                                  (SEQ ID NO: 41)
5'-AGATCTCAATCGGGTTACCCGATACCGAC-3'

Reverse primer:
                                  (SEQ ID NO: 42)
5'-CATATGTATATCTCCTTCTTATACTTAAC-3'
```

Enzyme for PCR: KOD-Plus-Neo (Toyobo Co., Ltd.)
Reaction conditions: 25 cycles each involving 98° C. for 10 seconds and 68° C. for 3 minutes and 20 seconds <1-3-2> Brev Protein DNA containing no DNA encoding the PgsA protein was amplified by PCR under conditions given below using the pCDF-pgsA-*indica* recombinant vector of Example 1(2) as a template. This amplified fragment was designated as DNA fragment 17. Subsequently, DNA fragment 15 of this Example 4(1)[1-2] and DNA fragment 17 were ligated using In-Fusion HD Cloning Kit (Takara Bio Inc.) according to the attached instruction manual. The resulting vector was designated as a pCDF-brev-*indica* recombinant vector.

<<PCR Conditions for Amplification of pCDFDuet-1 Plasmid-Derived DNA Having Insert of DNA Encoding Amino Acid Sequence of *B. Indica*-Derived β-fructofuranosidase>>
Template: pCDF-pgsA-*indica* recombinant vector of Example 1(2)

```
                                  (SEQ ID NO: 43)
Forward primer: 5'-AGATCCTCGGGTTACCCGATACCGA-3'

(SEQ ID NO: 44)
Reverse primer: 5'-ATGTATATCTCCTTCTTATACTTAACT-3'
```

Enzyme for PCR: KOD-Plus-Neo (Toyobo Co., Ltd.)
Reaction conditions: 25 cycles each involving 98° C. for 10 seconds and 68° C. for 3 minutes and 20 seconds (2) Enzymatic Reaction and Confirmation of Saccharide Composition The pCDF-capA_opti-*indica* recombinant vector and the pCDF-brev-*indica* recombinant vector of this Example 4(1) were each transferred to *E. coli* by the method described in Example 1(5), and the obtained recombinant *E. coli* was cultured. Subsequently, the enzymatic reaction of the β-fructofuranosidase was performed by the method described in Example 2(1) using the culture solution of each recombinant *E. coli*. Then, the proportion of each saccharide contained in the reaction solution was measured by the method described in Example 2(2) to calculate the amount of oligosaccharides formed, the rate of formation of oligosaccharides, the amount of sucrose consumed, and the rate of consumption of sucrose. The results are shown in Table 3. For comparison, Table 3 also shows the results about the reaction solutions of the *E. coli* transformed with the pCDF-*indica* recombinant vector and the pCDF-pgsA-*indica* recombinant vector described in Table 1.

TABLE 3

| Anchor protein | Recombinant vector | Bacterial cell weight | Amount of oligosaccharides formed (mg) | Amount of sucrose consumed (mg) | Rate of formation of oligosaccharides (%) (Amount of oligosaccharides formed/ Bacterial cell weight) × 100 | Rate of consumption of sucrose (%) (Amount of sucrose consumed/ Bacterial cell weight) × 100 |
|---|---|---|---|---|---|---|
| None (intracellular expression system) | pCDF-indica | 60.4 | 7.2 | 18.7 | 11.9 | 30.9 |
| PgsA | pCDF-pgsA-indica | 38.6 | 30.3 | 104.2 | 78.6 | 269.9 |
| CapA | pCDF-capA_opti-indica | 24.4 | 76 | 319 | 312.2 | 1308.9 |
| brev | pCDF-brev-indica | 53.1 | 1 | 3 | 1.0 | 5.0 |

As shown in Table 3, the rate of formation of oligosaccharides was 11.9% in the reaction solution of the *E. coli* transformed with the pCDF-*indica* recombinant vector whereas the rate of formation of oligosaccharides was 78.6% in the reaction solution of the *E. coli* transformed with the pCDF-pgsA-*indica* recombinant vector, 312.2% in the reaction solution of the *E. coli* transformed with the pCDF-capA_opti-*indica* recombinant vector, and 1.0% in the reaction solution of the *E. coli* transformed with the pCDF-brev-*indica* recombinant vector. In short, as compared with the case of using the pCDF-*indica* recombinant vector, the rate of formation of oligosaccharides was at least 6.6 times larger in the case of using the pCDF-pgsA-*indica* recombinant vector and at least 26.2 times larger in the case of using the pCDF-capA_opti-*indica* recombinant vector, whereas the rate of formation of oligosaccharides was as small as approximately 0.08 times in the case of using the pCDF-brev-*indica* recombinant vector.

It was found that the expression of the β-fructofuranosidase with the brev protein on the cell surface of *E. coli* reduces the efficiency of oligosaccharide formation as compared with the intracellular expression thereof, whereas the expression of the β-fructofuranosidase with the PgsA protein or the CapA protein on the cell surface of *E. coli* remarkably enhances the efficiency of oligosaccharide formation as compared with the intracellular expression thereof. These results demonstrated that a fructose-added carbohydrate can be efficiently produced by expressing an anchor protein comprising an amino acid sequence having 45% or higher identity to the amino acid sequence of PgsA protein or the amino acid sequence of CapA protein, and a β-fructofuranosidase as one polypeptide.

<Example 5> Study on Host

The effect of being able to efficiently produce a fructose-added carbohydrate by expressing an anchor protein for expression on the cell surface and a β-fructofuranosidase as one polypeptide was studied for whether or not to be exerted irrespective of the type of a host. Specifically, *Bacillus subtilis* from which the PgsA protein was derived and *Bacillus megaterium* from which the CapA protein was derived were examined as hosts.

(1) In the Case of Using *Bacillus subtilis* as Host
[1-1] Preparation of Recombinant Vector
DNA encoding the amino acid sequences of the PgsA protein and the *B. Indica*-derived β-fructofuranosidase was amplified by PCR under conditions given below. This amplified fragment was designated as DNA fragment 18.
<<PCR Conditions for Amplification of DNA Encoding Amino Acid Sequences of PgsA Protein and *B. Indica*-Derived β-fructofuranosidase>>
Template: pCDF-pgsA-*indica* recombinant vector of Example 1(2)

```
Forward primer:
                                    (SEQ ID NO: 45)
5'-AAGGAGGAAGGATCAATGAAAAAAGAACTGAGCTTTCATG-3'

Reverse primer:
                                    (SEQ ID NO: 46)
5'-CCCGGGGACGTCGACTTACTGGCCGTTCGTGACACCATGG-3'
```

Enzyme for PCR: KOD-Plus-Neo (Toyobo Co., Ltd.)
Reaction conditions: 25 cycles each involving 95° C. for 20 seconds, 50° C. for 30 seconds, and 68° C. for 2 minutes Primers of SEQ ID NO: 47 and SEQ ID NO: 48 given below were designed on the basis of the nucleotide sequence of a secretory expression vector pHT43 plasmid for *Bacillus subtilis* (MoBiTec GmbH), and pHT43 plasmid-derived DNA was amplified by PCR under conditions given below. This amplified fragment was designated as DNA fragment 19.

<<PCR Conditions for Amplification of pHT43 Plasmid-Derived DNA>>
Template: pHT43 plasmid (MoBiTec GmbH)

```
Forward primer:
                                    (SEQ ID NO: 47)
5'-GTCGACGTCCCCGGGGCAGCCCGCCTAATG-3'

Reverse primer:
                                    (SEQ ID NO: 48)
5'-TGATCCTTCCTCCTTTAATTGGGAATTGTT-3'
```

Enzyme for PCR: KOD-Plus-Neo (Toyobo Co., Ltd.)
Reaction conditions: 25 cycles each involving 95° C. for 20 seconds, 68° C. for 5 minutes, and 68° C. for 5 minutes Subsequently, DNA fragment 18 and DNA fragment 19 were ligated using In-Fusion HD Cloning Kit (Takara Bio Inc.) according to the attached instruction manual. The resulting vector was designated as a pHT43-pgsA-*indica* recombinant vector.
[1-2] Preparation of Transformant
The pHT43-pgsA-*indica* recombinant vector of this Example 5(1)[1-1] was transferred to *E. coli* by the method described in Example 1(5), and the recombinant *E. coli* was cultured. Then, the pHT43-pgsA-*indica* recombinant vector was recovered from the recombinant *E. coli*. The recovered pHT43-pgsA-*indica* recombinant vector and a pHT43 plasmid (MoBiTec GmbH) were each transferred to a *Bacillus subtilis* RIK1285 strain (*B. subtilis* Secretory Protein Expression System; Takara Bio Inc.) by electroporation to obtain transformants. Each of these transformants was used as recombinant *B. subtilis*. The electroporation was performed by the following procedures <1> to <8> using GENE PULSER II (Bio-Rad Laboratories, Inc.).
<1> An appropriate amount from a glycerol stock of *Bacillus subtilis* RIK1285 (*B. subtilis* Secretory Protein Expression System; Takara Bio Inc.) was spread over an LB plate and cultured overnight (approximately 16 hours) at 37° C. Then, a single colony was poked into a 250 mL flask containing 25 mL of an LB medium and precultured overnight (approximately 16 hours) at 28° C. to prepare a preculture solution.
<2> An LB medium supplemented with sorbitol (final concentration: 0.5 M) was prepared and used as a main culture medium. 5 mL of the preculture solution was added to a 250 mL Erlenmeyer flask containing 50 mL of the main culture medium, followed by main culture at 220 rpm at 37° C. to prepare a main culture solution. The main culture was performed until the value of turbidity reached the stationary phase (OD600=0.85 to 0.95).
<3> The Erlenmeyer flask of the main culture solution was left in ice for 10 minutes or longer and then centrifuged at 5000×g at 4° C. for 10 minutes. After removal of the supernatant, the bacterial cells were washed four times with ice-cold Solution A (0.5 M sorbitol, 0.5 M mannitol, 0.5 M trehalose, and 10% glycerol).
<4> Subsequently, the bacterial cells were suspended in an appropriate amount of Solution A. Then, 60 μL each of the cell suspensions was dispensed and stored at −80° C. The resultant was used as bacterial cells for electroporation.
<5> The bacterial cells for electroporation were thawed in ice. An appropriate amount of the pHT43-pgsA-*indica* recombinant vector as a sample, or a pHT43 plasmid (MoBiTec GmbH) as a control was added to the cells, which were then transferred to ice-cold cuvette with 0.1 cm gap and left for 1 to 1.5 minutes.

<6> After application of a pulse at 22 KV/cm (25 μF, 200Ω), 1 mL of Solution B (LB medium containing 0.5 M sorbitol and 0.38 M mannitol) was added to the cells, followed by mild shake culture at 37° C. for 3 hours.

<7> The culture solution was centrifuged at 3500 rpm for 5 minutes to remove the supernatant. The cells were suspended by the addition of 100 μL of Solution B, and the cell suspension was applied to an LB plate containing chloramphenicol (final concentration; 5 μg/mL) and cultured overnight at 37° C.

<8> Colonies appearing on the LB plate were added to 1 mL of an L medium containing chloramphenicol (final concentration: 5 μg/mL) and isopropyl-β-thiogalactopyranoside (IPTG) (final concentration: 1 mM) and gyratory-cultured at 220 rpm at 30° C. for 24 hours to prepare a recombinant *B. subtilis* culture solution.

[1-4] Enzymatic Reaction and Confirmation of Saccharide Composition

A 0.04 M potassium phosphate buffer containing 45 (w/w) % sucrose was prepared and used as a 45% sucrose solution. The bacterial cells were recovered by the centrifugation of each recombinant *B. subtilis* culture solution of this Example 5(1)[1-2]<8> at 3500 rpm at 4° C. for 10 minutes and suspended in 500 μL of the 45% sucrose solution. This suspension was shaken at 220 rpm at 30° C. for 24 hours for the enzymatic reaction of the β-fructofuranosidase. Subsequently, the reaction solution was diluted 25-fold with a 50% aqueous acetonitrile solution and used as an HPLC sample. Next, the HPLC sample was subjected to HPLC under conditions given below to confirm saccharide composition. The results are shown in FIG. 2.

<<HPLC Analysis Conditions>>

Column: Cosmosil Sugar-D 4.6×150 mm

Eluent: aqueous acetonitrile solution (0 to 9 minutes: 72.5 to 57.5%, 9 to 11 minutes: 72.5%)

Column temperature: 25° C.

Flow rate: 1.5 mL/min

Injection volume: 1.5 μL

Detection: corona charged aerosol detector (CAD; Thermo Fisher Scientific Inc.)

As shown in FIG. 2, the reaction solution of the recombinant *B. subtilis* obtained by transformation with the pHT43-pgsA-*indica* recombinant vector and the reaction solution of the recombinant *B. subtilis* (control) obtained by transformation with the pHT43 plasmid produced almost the same shapes of HPLC charts and both were confirmed to hardly form trisaccharide or higher oligosaccharides, glucose, or fructose. These results demonstrated that a fructose-added carbohydrate cannot be efficiently produced by expressing an anchor protein for expression on the cell surface and a β-fructofuranosidase as one polypeptide in *Bacillus subtilis*.

(2) In the Case of Using *Bacillus megaterium* as Host

[2-1] Preparation of Recombinant Vector

DNA encoding the amino acid sequences of the CapA protein and the *B. Indica*-derived β-fructofuranosidase was amplified by PCR under conditions given below. This amplified fragment was designated as DNA fragment 20.

<<PCR Conditions for Amplification of DNA Encoding Amino Acid Sequences of CapA Protein and *B. Indica*-Derived β-fructofuranosidase>>

Template: pCDF-capA_opti-*indica* recombinant vector of Example 4(1)

```
Forward primer:
                                       (SEQ ID NO: 49)
5'-AGGGGGAAATGACAAATGAAAGAAAAGAAACTGAACTTCC-3'

Reverse primer:
                                       (SEQ ID NO: 50)
5'-ACTAGTTTGGACCATTTACTGGCCGTTCGTGACACCATGG-3'
```

Enzyme for PCR: KOD-Plus-Neo (Toyobo Co., Ltd.)

Reaction conditions: 21 cycles each involving 94° C. for 15 seconds, 58° C. for 20 seconds, and 68° C. for 3 minutes Primers of SEQ ID NO: 51 and SEQ ID NO: 52 given below were designed on the basis of the nucleotide sequence of an expression vector pWH1520 plasmid for *Bacillus megaterium* (MoBiTec GmbH), and pWH1520 plasmid-derived DNA was amplified by PCR under conditions given below. This amplified fragment was designated as DNA fragment 21.

<<PCR Conditions for Amplification of DNA of pWH1520 Plasmid>>

Template: pWH1520 plasmid (MoBiTec GmbH)

```
Forward primer:
                                       (SEQ ID NO: 51)
5'-ATGGTCCAAACTAGTACTAATAAAATTAAT-3'

Reverse primer:
                                       (SEQ ID NO: 52)
5'-TTGTCATTTCCCCCTTTGATTTAAGTGAAC-3'
```

Enzyme for PCR: KOD-Plus-Neo (Toyobo Co., Ltd.)

Reaction conditions: 35 cycles each involving 94° C. for 15 seconds and 68° C. for 9 minutes Subsequently, DNA fragment 20 and DNA fragment 21 were ligated using In-Fusion HD Cloning Kit (Takara Bio Inc.) according to the attached instruction manual. The resulting vector was designated as a pWH1520-capA_opti-*indica* recombinant vector.

[2-2] Preparation of Transformant

The pWH1520-capA_opti-*indica* recombinant vector of this Example 5(2)[2-1] was transferred to *E. coli* by the method described in Example 1(5), and the recombinant *E. coli* was cultured. Then, the pWH1520-capA_opti-*indica* recombinant vector was recovered from the recombinant *E. coli*. The recovered pWH1520-capA_opti-*indica* recombinant vector and a control pWH1520 plasmid (MoBiTec GmbH) were each transferred to *Bacillus megaterium* by the protoplast method to obtain transformants. Each of these transformants was used as recombinant *B. megaterium*. The protoplast method was performed using *Bacillus megaterium* Protoplast (MoBiTec GmbH) according to the attached instruction manual. Each obtained recombinant *B. megaterium* was added to 1 mL of an LB medium containing tetracycline (final concentration: 10 μg/mL) and gyratory-cultured at 220 rpm at 30° C. for 6 hours. Then, xylose (final concentration: 0.5 (w/w) %) was added to the medium, followed by further gyratory culture for 18 hours under the same conditions as above to prepare a recombinant *B. megaterium* culture solution.

[2-3] Enzymatic Reaction and Confirmation of Saccharide Composition

Each recombinant *B. megaterium* culture solution of this Example 5(2)[2-2] was subjected to enzymatic reaction by the method described in this Example 5(1)[1-4], and the saccharide composition of the reaction solution was then confirmed. The results are shown in FIG. 3.

As shown in FIG. 3, the reaction solution of the recombinant *B. megaterium* obtained by transformation with the pWH1520-capA_opti-*indica* recombinant vector and the reaction solution of the recombinant *B. megaterium* obtained by transformation with the pWH1520 plasmid produced almost the same shapes of HPLC charts and both were confirmed to hardly form trisaccharide or higher oligosaccharides, glucose, or fructose. These results demonstrated that a fructose-added carbohydrate cannot be efficiently produced by expressing an anchor protein for expression on the cell surface and a β-fructofuranosidase as one polypeptide in *Bacillus megaterium*.

The results of this Example 5(1)[1-4] and this Example 5(2)[2-3] demonstrated that a fructose-added carbohydrate cannot be efficiently produced by expressing an anchor protein for expression on the cell surface and a β-fructofuranosidase as one polypeptide with *Bacillus subtilis* or *Bacillus megaterium* as a host, though the PgsA protein is derived from *Bacillus subtilis* and the CapA protein is derived from *Bacillus megaterium*.

Yeasts frequently used in conventional protein expression have an endogenous β-fructofuranosidase and therefore require using their variants deficient in the activity (sucrose utilization) of the endogenous β-fructofuranosidase for producing a fructose-added carbohydrate by the transfer of a foreign β-fructofuranosidase (e.g., Japanese Patent No. 3628336, page 24 (3)). Thus, the yeasts have poor versatility or handleability as hosts for the method for producing a fructose-added carbohydrate using a β-fructofuranosidase.

The results described above demonstrated that *E. coli* is most suitable as a host in the method for producing a fructose-added carbohydrate using a microorganism expressing an anchor protein for expression on the cell surface and a β-fructofuranosidase as one polypeptide.

<Example 6> Study on Receptor Substrate

A substance capable of receiving transfer of fructose (receptor substrate) by a β-fructofuranosidase expressed by *E. coli* as one polypeptide in the form of a fusion protein with an anchor protein for expression on the cell surface was studied. Specifically, a monosaccharide, a disaccharide, a glycoside, and a non-carbohydrate substance hydroquinone were examined for whether or not to be able to serve as an receptor substrate.

(1) Monosaccharide, Disaccharide, and Glycoside
[1-1] Enzymatic Reaction

The culture solution of the recombinant *E. coli* of Example 1(5) obtained by transformation with the pCDF-pgsA-*indica* recombinant vector of Example 1(2) was centrifuged at 12000 rpm at 4° C. for 5 minutes to collect bacterial cells. Then, approximately 10 mg (wet weight) of the bacterial cells was prepared. Sucrose (granulated sugar; Mitsui Sugar Co., Ltd.) was prepared as a donor substrate of a fructose residue, while monosaccharides (D(+)-xylose (Wako Pure Chemical Industries, Ltd.) and L(+)-arabinose (Wako Pure Chemical Industries, Ltd.)), disaccharides (melibiose (Wako Pure Chemical Industries, Ltd.) and lactose monohydrate (Wako Pure Chemical Industries, Ltd.)), and a glycoside (α-methyl-D(+)-glucoside (Wako Pure Chemical Industries, Ltd.)) were prepared as receptor substrates. Substrate solution Nos. 1 to 5 were prepared according to the composition shown in Table 4. The solvent used for the substrate solutions was a 0.04 M sodium phosphate buffer (pH 7.0). 10 mg of the wet bacterial cells was suspended by the addition of 200 μL each of substrate solution Nos. 1 to 5, and each suspension was shaken at 200 rpm at 40° C. for 1 hour for the enzymatic reaction of the β-fructofuranosidase to obtain reaction solutions. The reaction solutions obtained by the addition of substrate solution Nos. 1 to 5 were designated as reaction solution Nos. 1 to 5, respectively.

TABLE 4

| | Substrate solution No. 1 | Substrate solution No. 2 | Substrate solution No. 3 | Substrate solution No. 4 | Substrate solution No. 5 |
|---|---|---|---|---|---|
| Solvent | 0.04M sodium phosphate buffer (pH7.0) | | | | |
| Donor substrate (w/w) % | Sucrose; 50.8 | Sucrose; 50.6 | Sucrose; 49.1 | Sucrose; 66.8 | Sucrose; 52.1 |
| Receptor substrate (w/w) % | Xylose; 49.2 | Arabinose; 49.4 | Melibiose; 50.9 | Lactose monohydrate; 33.2 | α-Methyl-D(+)-glucoside; 47.9 |
| Substrate concentration (w/w) % | 33.3 | 33.3 | 33.3 | 27.3 | 33.3 |

[1-2] Confirmation of Saccharide Composition

50 μL each of reaction solution Nos. 1 to 5 of this Example 6(1)[1-1] was diluted by the addition of 450 μL of water and 500 μL of acetonitrile and then heated at 70° C. for 10 minutes. Subsequently, each supernatant was recovered by centrifugation at 15000×g at 25° C. for 10 minutes and filtered through a filter having a pore size of 0.45 μm. Each obtained filtrate was used as an HPLC sample. This HPLC sample was subjected to HPLC under conditions given below to measure the proportion of each saccharide contained in the reaction solution. The proportion of each saccharide was calculated in percentage as a ratio of the area of each peak to the total area of all peaks detected. The results are shown in Table 5.

<<HPLC Conditions>>

Column: TOSOH TSKgel Amide 80 particle size: 5 μm (4.6φ×250 mm)

Eluent: aqueous acetonitrile solution (HPLC samples of reaction solution Nos. 1, 2, and 5: 78%, HPLC samples of reaction solution Nos. 3 and 4: 70%)

Column temperature: 70° C.

Flow rate: 1.0 mL/min

Injection volume: 20 μL

Detection: differential refractive index detector (RID; Showa Denko K.K.)

TABLE 5

| | | Proportion of each saccharide (%) | | | | | |
|---|---|---|---|---|---|---|---|
| | Saccharide derived from receptor substrate | | Saccharide derived from donor substrate | | | | |
| | Receptor substrate | Receptor substrate-derived oligosaccharide | D(+)-fructose | D(+)-glucose | Sucrose | Sucrose-derived oligosaccharide | Others |
| Reaction solution No. 1 | D(+)-xylose | 18.1 | 7.0 | 26.2 | 6.6 | 0.7 | — |
| | 41.4 | | | | | | |
| Reaction solution No. 2 | L(+)-arabinose | 27.9 | 3.2 | 24.9 | 4.5 | — | — |
| | 39.5 | | | | | | |
| Reaction solution No. 3 | Melibiose | 20.8 | 4.5 | 21.1 | 11.9 | 2.3 | 0.2 |
| | 39.2 | | | | | | |
| Reaction solution No. 4 | Lactose monohydrate | 18.9 | 6.1 | 24.4 | 25.0 | 3.6 | 1.1 |
| | 20.8 | | | | | | |
| Reaction solution No. 5 | α-methyl-D(+)-glucoside | 16.4 | 6.3 | 22.1 | 11.3 | 1.0 | — |
| | 42.9 | | | | | | |

As shown in Table 5, all of reaction solution Nos. 1 to 5 were confirmed to contain oligosaccharides derived from the receptor substrates. In short, reaction solution Nos. 1 to 5 were found to form oligosaccharides by the transfer of a fructose residue to D(+)-xylose, L(+)-arabinose, melibiose, lactose monohydrate, and α-methyl-D(+)-glucoside. These results demonstrated that a carbohydrate can serve as a receptor substrate for a β-fructofuranosidase expressed by E. coli as one polypeptide in the form of a fusion protein with an anchor protein for expression on the cell surface.

(2) Hydroquinone

[2-1] Enzymatic Reaction

Approximately 10 mg (wet weight of bacterial cells) of the culture solution of the recombinant E. coli of Example 1(5) obtained by transformation with the pCDF-pgsA-*indica* recombinant vector of Example 1(2) was prepared. Sucrose (granulated sugar; Mitsui Sugar Co., Ltd.) was prepared as a donor substrate of a fructose residue, while hydroquinone (Wako Pure Chemical Industries, Ltd.) was prepared as an receptor substrate. 342 mg of the sucrose (final concentration: 1 M) and 28 mg of the hydroquinone (final concentration: 0.25 M) were dissolved in 1 mL of a 50 mM acetate buffer (pH 6.0) to prepare a substrate solution. 10 mg of the wet bacterial cells was suspended by the addition of 500 μL of the substrate solution. Then, this suspension was shaken at 200 rpm at 40° C. for 1 hour for the enzymatic reaction of the β-fructofuranosidase and used as a sample reaction solution. Also, control solution Nos. 1 to 3 were prepared according to composition given below and similarly shaken at 200 rpm at 40° C. for 1 hour to obtain control reaction solution Nos. 1 to 3.

Control solution No. 1: 10 mg of the wet bacterial cells supplemented with 500 μL of a 50 mM acetate buffer (pH 6.0)

Control solution No. 2: substrate solution alone (free from the wet bacterial cells)

Control solution No. 3: 10 mg of the wet bacterial cells supplemented with 500 μL of a 50 mM acetate buffer (pH 6.0) containing sucrose (final concentration: 1 M).

[2-2] Confirmation of Substance Contained in Reaction Solution

The sample reaction solution of this Example 6(2)[2-1] and control reaction solution Nos. 1 to 3 were each subjected to HPLC by the method described in this Example 6(1)[1-2] to confirm substances contained in the reaction solutions. However, the HPLC conditions were as described below. The results are shown in FIG. 4. Hydroquinone and products derived therefrom are mainly detected by UV detection at 280 nm, while saccharides and products derived therefrom are mainly detected by ELSD.

<<HPLC Conditions>>

Column: Imtakt Unison UK-Amino

Eluent: aqueous acetonitrile solution (0 to 30 minutes: 98 to 70% gradient)

Column temperature: 60° C.

Flow rate: 0.4 mL/min

Injection volume: 1 μL

Detection: UV detector (280 nm) and evaporative light scattering detector (ELSD)

As indicated by the arrows in the uppermost HPLC charts of FIG. 4, peaks were detected only in the sample reaction solution at retention times of approximately 12 minutes, approximately 19 minutes, and approximately 24 minutes. The peaks at reaction times similar thereto were not detected in control reaction solution No. 1, demonstrating that the peaks were not derived from the bacterial cells. These peaks were not detected in control reaction solution No. 2, demonstrating that the peaks were not derived from hydroquinone or sucrose. These peaks were not detected in control reaction solution No. 3, demonstrating that the peaks were not derived from products formed by the action of the β-fructofuranosidase on sucrose (glucose, fructose, oligosaccharides such as kestose, etc.). In short, the sample reaction solution was found to form a glycoside by the transfer of fructose to hydroquinone. These results demonstrated that a non-carbohydrate substance can also serve as a receptor substrate for a β-fructofuranosidase expressed by E. coli as one polypeptide in the form of a fusion protein with an anchor protein for expression on the cell surface.

The results of this Example 6(1)[1-2] and this Example 6(2)[2-2] demonstrated that a fructose-added carbohydrate can be produced using a β-fructofuranosidase expressed by E. coli as one polypeptide in the form of a fusion protein with an anchor protein for expression on the cell surface, with a carbohydrate or a non-carbohydrate substance as a receptor substrate.

The invention claimed is:

1. An *E. coli* expressing a fusion protein comprising:
   (a) a protein of SEQ ID NO: 34, and
   (b) a β-fructofuranosidase, wherein the β-fructofuranosidase consists of SEQ ID NO: 2.

2. A method for producing a polypeptide comprising a β-fructofuranosidase, comprising
   (I) a step of expressing a fusion protein of SEQ ID NO: 34 and a β-fructofuranosidase in an *E. coli* comprising a polynucleotide encoding the fusion protein, wherein the β-fructofuranosidase consists of SEQ ID NO: 2, and
   (II) a step of extracting or purifying the polypeptide from the *E. coli* of step (I).

3. An *E. coli* comprising a polynucleotide encoding a fusion protein comprising:
   (a) a protein of SEQ ID NO: 34, and
   (b) a β-fructofuranosidase, wherein the β-fructofuranosidase consists of SEQ ID NO: 2.

* * * * *

SEQUENCE LISTING

<160> NUMBER OF SEQ ID NOS: 52

<210> SEQ ID NO 1
<211> LENGTH: 1605
<212> TYPE: DNA
<213> ORGANISM: Beijerinckia indica

<400> SEQUENCE: 1

```
atggcaagtc gatcgtttaa tgtttgtata cgtagcctca tcgcgggctc gcttctgact     60
gccacagcac tgtccgctca ggctcaatcg ggttacccga taccgactcc gcattcggga    120
caagcctatg atccatttgc agattttacc gccaaatgga cgcgcgccaa tgcccgtcaa    180
atcaaggcgc aatcacatgt cccggtgtca cccgatcaga attcgctgcc gctcaatctg    240
acgatgcccg atatccctgc cgatttcccg caaaccaacc cggacgtgtg ggtgtgggat    300
acgtggcctc tcgccgatgt gcatggcaat cagctgagct tccaggggtg ggaggtcatt    360
ttctcgctga ccgctgatcc gcatgccggt tatgttttcg atgatcgcca cgttcacgca    420
cgtatcggct tcttttatcg caaggccgga attcccgcga accagcgccc gattgatggc    480
ggctggatct atggcgggca tttgttcccg gatggtagca gcgtcaaagt cttcggtaac    540
gtccccatga cgcaaaacgc ggaatggtcc ggcggcgccc gcttcgtggg cggcccttat    600
gctgatggcc cgcaacacgc ctacctgaag aacaacaacg tcagcctcta ttacacggcg    660
acatcgttca accgtaatgc tcagggcggt aacatcacac cgccgatcgc catcatctcg    720
cgcgcggatg gacaaattca agcagatgat aagcatgtgt ggttcacggg attcgatcaa    780
catctcccgc tgctcgcacc cgacggcaaa tattatcaga ccggtcagca gaacgagttc    840
ttctccttcc gcgatcccta tgtcttcctt gaccccgctc atccgggcaa gaccttcatg    900
gtcttcgaag gcaataccgc cgtgcagcgc ggctcccgct cctgcaccga ggcagatctc    960
ggatattctc ccaatgaccc gaacaaagaa gacctgaatg cggtcatgga ctccggagcc   1020
atttaccaaa tggccaatgt cggtcttgcc gtggcgacga acgatgaact gacgcagtgg   1080
aagttcctgc cgccgatcct gtccggtaat tgcgtgaacg atcagaccga acgtcctcag   1140
atctatctga aggatggaaa atattacctg ttcacgatca gccaccgcac gacctatgcg   1200
gcgggcgtcg atgggccgga cggcgtctat ggcttcgtcg gtgatggcat tcgcagcgac   1260
ttcattcccc tgaatggcct cagcggtctc acgctcggca acccgaccga tctctatcag   1320
ccggccggcg ctccttacgc cttgaatcca aaccaaaatc ctcggacgtt ccagtcctat   1380
tcgcattatg tcatgccggg cggcctcgtt gaatcgttta tcgatgccat cggccctcgt   1440
cgcggtggcg cgctggctcc gacggtgaag atcaacatca acggaacttc taccatcctc   1500
gacaggacct atggcaatgc cggattgggt ggctatggcg acatcccggc caatcttccc   1560
gcgcttggcc aagttaatgg ccatggtgtc acgaacggcc agtaa                   1605
```

<210> SEQ ID NO 2
<211> LENGTH: 534
<212> TYPE: PRT
<213> ORGANISM: Beijerinckia indica

<400> SEQUENCE: 2

```
Met Ala Ser Arg Ser Phe Asn Val Cys Ile Arg Ser Leu Ile Ala Gly
1               5                   10                  15

Ser Leu Leu Thr Ala Thr Ala Leu Ser Ala Gln Ala Gln Ser Gly Tyr
            20                  25                  30

Pro Ile Pro Thr Pro His Ser Gly Gln Ala Tyr Asp Pro Phe Ala Asp
```

```
             35                  40                  45
Phe Thr Ala Lys Trp Thr Arg Ala Asn Ala Arg Gln Ile Lys Ala Gln
 50                  55                  60

Ser His Val Pro Val Ser Pro Asp Gln Asn Ser Leu Pro Leu Asn Leu
 65                  70                  75                  80

Thr Met Pro Asp Ile Pro Ala Asp Phe Pro Gln Thr Asn Pro Asp Val
                     85                  90                  95

Trp Val Trp Asp Thr Trp Pro Leu Ala Asp Val His Gly Asn Gln Leu
                    100                 105                 110

Ser Phe Gln Gly Trp Glu Val Ile Phe Ser Leu Thr Ala Asp Pro His
            115                 120                 125

Ala Gly Tyr Val Phe Asp Asp Arg His Val His Ala Arg Ile Gly Phe
            130                 135                 140

Phe Tyr Arg Lys Ala Gly Ile Pro Ala Asn Gln Arg Pro Ile Asp Gly
145                 150                 155                 160

Gly Trp Ile Tyr Gly Gly His Leu Phe Pro Asp Gly Ser Ser Val Lys
                    165                 170                 175

Val Phe Gly Asn Val Pro Met Thr Gln Asn Ala Glu Trp Ser Gly Gly
                    180                 185                 190

Ala Arg Phe Val Gly Gly Pro Tyr Ala Asp Gly Pro Gln His Ala Tyr
            195                 200                 205

Leu Lys Asn Asn Val Ser Leu Tyr Tyr Thr Ala Thr Ser Phe Asn
210                 215                 220

Arg Asn Ala Gln Gly Gly Asn Ile Thr Pro Ile Ala Ile Ser
225                 230                 235                 240

Arg Ala Asp Gly Gln Ile Gln Ala Asp Lys His Val Trp Phe Thr
                    245                 250                 255

Gly Phe Asp Gln His Leu Pro Leu Leu Ala Pro Asp Gly Lys Tyr Tyr
                    260                 265                 270

Gln Thr Gly Gln Gln Asn Glu Phe Phe Ser Phe Arg Asp Pro Tyr Val
            275                 280                 285

Phe Leu Asp Pro Ala His Pro Gly Lys Thr Phe Met Val Phe Glu Gly
290                 295                 300

Asn Thr Ala Val Gln Arg Gly Ser Arg Ser Cys Thr Glu Ala Asp Leu
305                 310                 315                 320

Gly Tyr Ser Pro Asn Asp Pro Asn Lys Glu Asp Leu Asn Ala Val Met
                    325                 330                 335

Asp Ser Gly Ala Ile Tyr Gln Met Ala Asn Val Gly Leu Ala Val Ala
            340                 345                 350

Thr Asn Asp Glu Leu Thr Gln Trp Lys Phe Leu Pro Pro Ile Leu Ser
            355                 360                 365

Gly Asn Cys Val Asn Asp Gln Thr Glu Arg Pro Gln Ile Tyr Leu Lys
            370                 375                 380

Asp Gly Lys Tyr Tyr Leu Phe Thr Ile Ser His Arg Thr Thr Tyr Ala
385                 390                 395                 400

Ala Gly Val Asp Gly Pro Asp Gly Val Tyr Gly Phe Val Gly Asp Gly
                    405                 410                 415

Ile Arg Ser Asp Phe Ile Pro Leu Asn Gly Leu Ser Gly Leu Thr Leu
                    420                 425                 430

Gly Asn Pro Thr Asp Leu Tyr Gln Pro Ala Gly Ala Pro Tyr Ala Leu
            435                 440                 445

Asn Pro Asn Gln Asn Pro Arg Thr Phe Gln Ser Tyr Ser His Tyr Val
            450                 455                 460
```

```
Met Pro Gly Gly Leu Val Glu Ser Phe Ile Asp Ala Ile Gly Pro Arg
465                 470                 475                 480

Arg Gly Gly Ala Leu Ala Pro Thr Val Lys Ile Asn Ile Asn Gly Thr
                485                 490                 495

Ser Thr Ile Leu Asp Arg Thr Tyr Gly Asn Ala Gly Leu Gly Gly Tyr
            500                 505                 510

Gly Asp Ile Pro Ala Asn Leu Pro Ala Leu Gly Gln Val Asn Gly His
        515                 520                 525

Gly Val Thr Asn Gly Gln
        530
```

```
<210> SEQ ID NO 3
<211> LENGTH: 31
<212> TYPE: DNA
<213> ORGANISM: Artificial Sequence
<220> FEATURE:
<223> OTHER INFORMATION: forward primer

<400> SEQUENCE: 3
atggcaagtc gatcgtttaa tgtttgtata c                              31

<210> SEQ ID NO 4
<211> LENGTH: 33
<212> TYPE: DNA
<213> ORGANISM: Artificial Sequence
<220> FEATURE:
<223> OTHER INFORMATION: reverse primer

<400> SEQUENCE: 4
tttaccagac tcgagttact ggccgttcgt gac                            33

<210> SEQ ID NO 5
<211> LENGTH: 1143
<212> TYPE: DNA
<213> ORGANISM: Bacillus subtilis

<400> SEQUENCE: 5
atgaaaaaag aactgagctt tcatgaaaag ctgctaaagc tgacaaaaca gcaaaaaaag      60
aaaaccaata agcacgtatt tattgccatt ccgatcgttt ttgtccttat gttcgctttc     120
atgtgggcgg aaaagcgga aacgccgaag gtcaaaacgt attctgacga cgtactctca     180
gcctcatttg taggcgatat tatgatggga cgctatgttg aaaaagtaac ggagcaaaaa     240
ggggcagaca gtattttca atatgttgaa ccgatcttta gagcctcgga ttatgtagca     300
ggaaactttg aaaacccggt aacctatcaa aagaattata acaagcaga taaagagatt      360 catctgcaga cgaataagga atcagtgaaa gtcttgaagg atatgaattt cacggttctc     420
aacagcgcca acaaccacgc aatggattac ggcgttcagg gcatgaaaga tacgcttgga     480
gaatttgcga agcaaaatct tgatatcgtt ggagcgggat acagcttaag tgatgcgaaa     540
agaaaatttt cgtaccagaa agtcaacggg gtaacgattg cgacgcttgg ctttaccgat     600
gtgtccggga aggtttcgc ggctaaaaag aatacgccgg gcgtgctgcc cgcagatcct      660
gaaatcttca tccctatgat ttcagaagcg aaaaacatg cggacattgt tgttgtgcag      720
tcacactggg acaagagta tgacaatgat ccaaatgacc gccagcgcca gcttgcaaga     780
gccatgtctg atgcgggagc tgacatcatc gtcggccatc accgcacgt cttagaaccg      840 attgaagtat ataacggaac cgtcattttc tacagcctcg gcaactttgt ctttgaccaa     900
ggctggacga gaacaagaga cagtgcactg gttcagtatc acctgaagaa aaatggaaca     960
```

-continued

```
ggacgctttg aagtgacacc gatcgatatc catgaagcga cacctgcgcc tgtgaaaaaa    1020
gacagcctta aacagaaaac cattattcgc gaactgacga agactctaa tttcgcttgg     1080 aaagtagaag acggaaaact gacgtttgat attgatcata gtgacaaact aaaatctaaa    1140
taa                                                                  1143
```

<210> SEQ ID NO 6
<211> LENGTH: 380
<212> TYPE: PRT
<213> ORGANISM: Bacillus subtilis

<400> SEQUENCE: 6

```
Met Lys Lys Glu Leu Ser Phe His Glu Lys Leu Leu Lys Leu Thr Lys
1               5                   10                  15

Gln Gln Lys Lys Lys Thr Asn Lys His Val Phe Ile Ala Ile Pro Ile
            20                  25                  30

Val Phe Val Leu Met Phe Ala Phe Met Trp Ala Gly Lys Ala Glu Thr
        35                  40                  45

Pro Lys Val Lys Thr Tyr Ser Asp Asp Val Leu Ser Ala Ser Phe Val
    50                  55                  60

Gly Asp Ile Met Met Gly Arg Tyr Val Glu Lys Val Thr Glu Gln Lys
65                  70                  75                  80

Gly Ala Asp Ser Ile Phe Gln Tyr Val Glu Pro Ile Phe Arg Ala Ser
                85                  90                  95

Asp Tyr Val Ala Gly Asn Phe Glu Asn Pro Val Thr Tyr Gln Lys Asn
            100                 105                 110

Tyr Lys Gln Ala Asp Lys Glu Ile His Leu Gln Thr Asn Lys Glu Ser
        115                 120                 125

Val Lys Val Leu Lys Asp Met Asn Phe Thr Val Leu Asn Ser Ala Asn
    130                 135                 140

Asn His Ala Met Asp Tyr Gly Val Gln Gly Met Lys Asp Thr Leu Gly
145                 150                 155                 160

Glu Phe Ala Lys Gln Asn Leu Asp Ile Val Gly Ala Gly Tyr Ser Leu
                165                 170                 175

Ser Asp Ala Lys Lys Ile Ser Tyr Gln Lys Val Asn Gly Val Thr
            180                 185                 190

Ile Ala Thr Leu Gly Phe Thr Asp Val Ser Gly Lys Gly Phe Ala Ala
        195                 200                 205

Lys Lys Asn Thr Pro Gly Val Leu Pro Ala Asp Pro Glu Ile Phe Ile
    210                 215                 220

Pro Met Ile Ser Glu Ala Lys Lys His Ala Asp Ile Val Val Val Gln
225                 230                 235                 240

Ser His Trp Gly Gln Glu Tyr Asp Asn Asp Pro Asn Asp Arg Gln Arg
                245                 250                 255

Gln Leu Ala Arg Ala Met Ser Asp Ala Gly Ala Asp Ile Ile Val Gly
            260                 265                 270

His His Pro His Val Leu Glu Pro Ile Glu Val Tyr Asn Gly Thr Val
        275                 280                 285

Ile Phe Tyr Ser Leu Gly Asn Phe Val Phe Asp Gln Gly Trp Thr Arg
    290                 295                 300

Thr Arg Asp Ser Ala Leu Val Gln Tyr His Leu Lys Lys Asn Gly Thr
305                 310                 315                 320

Gly Arg Phe Glu Val Thr Pro Ile Asp Ile His Glu Ala Thr Pro Ala
                325                 330                 335
```

```
Pro Val Lys Lys Asp Ser Leu Lys Gln Lys Thr Ile Ile Arg Glu Leu
            340                 345                 350

Thr Lys Asp Ser Asn Phe Ala Trp Lys Val Glu Asp Gly Lys Leu Thr
        355                 360                 365

Phe Asp Ile Asp His Ser Asp Lys Leu Lys Ser Lys
    370                 375                 380

<210> SEQ ID NO 7
<211> LENGTH: 31
<212> TYPE: DNA
<213> ORGANISM: Artificial Sequence
<220> FEATURE:
<223> OTHER INFORMATION: forward primer

<400> SEQUENCE: 7
aaacatatga aaaagaact gagctttcat g                              31

<210> SEQ ID NO 8
<211> LENGTH: 33
<212> TYPE: DNA
<213> ORGANISM: Artificial Sequence
<220> FEATURE:
<223> OTHER INFORMATION: reverse primer

<400> SEQUENCE: 8
aaaagatctt ttagatttta gtttgtcact atg                           33

<210> SEQ ID NO 9
<211> LENGTH: 44
<212> TYPE: DNA
<213> ORGANISM: Artificial Sequence
<220> FEATURE:
<223> OTHER INFORMATION: forward primer

<400> SEQUENCE: 9
aaaggatcct cgggttaccc gataccgact ccgcattcgg gaca               44

<210> SEQ ID NO 10
<211> LENGTH: 42
<212> TYPE: DNA
<213> ORGANISM: Artificial Sequence
<220> FEATURE:
<223> OTHER INFORMATION: reverse primer

<400> SEQUENCE: 10 ccctcgagt tactggccgt tcgtgacacc atggccatta ac                  42

<210> SEQ ID NO 11
<211> LENGTH: 26
<212> TYPE: DNA
<213> ORGANISM: Artificial Sequence
<220> FEATURE:
<223> OTHER INFORMATION: forward primer

<400> SEQUENCE: 11
catatgtcgg gttacccgat accgac                                   26

<210> SEQ ID NO 12
<211> LENGTH: 28
<212> TYPE: DNA
<213> ORGANISM: Artificial Sequence
<220> FEATURE:
<223> OTHER INFORMATION: reverse primer

<400> SEQUENCE: 12
```
tatatctcct tcttatactt aactaata    28

<210> SEQ ID NO 13
<211> LENGTH: 33
<212> TYPE: DNA
<213> ORGANISM: Artificial Sequence
<220> FEATURE:
<223> OTHER INFORMATION: forward primer

<400> SEQUENCE: 13
gatggttcaa ctagttcggg ttacccgata ccg    33

<210> SEQ ID NO 14
<211> LENGTH: 32
<212> TYPE: DNA
<213> ORGANISM: Artificial Sequence
<220> FEATURE:
<223> OTHER INFORMATION: reverse primer

<400> SEQUENCE: 14
gtggtggtgc tcgagttact ggccgttcgt ga    32

<210> SEQ ID NO 15
<211> LENGTH: 35
<212> TYPE: DNA
<213> ORGANISM: Artificial Sequence
<220> FEATURE:
<223> OTHER INFORMATION: forward primer

<400> SEQUENCE: 15
ctcgagcacc accaccacca ccaccaccac taatt    35

<210> SEQ ID NO 16
<211> LENGTH: 21
<212> TYPE: DNA
<213> ORGANISM: Artificial Sequence
<220> FEATURE:
<223> OTHER INFORMATION: reverse primer

<400> SEQUENCE: 16
actagttgaa ccatccgatt t    21

<210> SEQ ID NO 17
<211> LENGTH: 1596
<212> TYPE: DNA
<213> ORGANISM: Burkholderia phymatum STM815

<400> SEQUENCE: 17
atgaacgttg gccaccaccc gcgggtcccc cggatcaccc cccggctgcg cgcgcacttc 60
ctgtcggcag cggtgctgtc ggctgttgcc ctaccggcgc tggctcagac tgcaacgcca 120
ggcttccccg cgccgacgcc gcactcgcag caggcatacg accccgagag cagtttcacg 180
atgcgctgga cccgtgccga catccgtcag atcaaggcgc agtcgcatgc cgcgacggcg 240
gcggacaaga actcgctgcc gctttcgctg accatgccgg acatcccgca ggatttcccg 300
ctgatcaatc cgaacgtctg ggtgtgggac acgtggccgc tggccgacat gcgggcgaac 360
cagctggcgt acaagggctg ggaggtgatc ttttcgctga cggccgatcc gcatgccggc 420
tatacgttcg acgaccgtca cgttcacgcg cgcatcggct tcttctaccg ccgcgcgggc 480
attcccgcat cgcagcgacc cgcgaacggc ggctggacct ggggcggcca tctgttcccg 540
gacggtgcga gcgtcaaggt attcggcacg tcgccgatga ccgacaacgc cgaatggtcg 600

-continued

```
ggctcggcgc gtctcacgca cggcgacaac gtcagcctct actacaccgc gacgtcgttc    660
aaccgttcgg ccccggcgg cgccgacatt acgccgccgc aggcgatcat acgcgcgcc     720
gacggtcaca tccacgccga cgacagtcat gtgtggttct caggcttcga cgatcaccag    780
gcattgctca agccggacgg cacctactac cagaccggcg agcagaacac ctacttctca    840
taccgggatc cgttcgtgtt catcgatccc gcgcatccag gcaagaccta catggtgttc    900
gaaggcaaca cgggcggtcc gcgcggcgcg cgcacctgta cggaagccga cctcggctat    960
gcgccgaacg atccgcaacg ggaagacctg aacgcggtga tgaactcggg cgcggcgtat   1020
cagaaggcca atgttggtct cgcggtcgcg acgaatccgc aactgaccga atggaagttc   1080
ctgccaccga tcctgtcggc gaactgcgtc gatgatcaga ccgagcgccc gcagatttac   1140
ctgaaggacg gcaagtacta cctgttcacg atcagccacc gcacaacgat ggcagcaggc   1200
gttgacggac cggacggtgt ctacggcttc gtcggcaacg gcatccgcag cgacttcttg   1260
ccgctgaacg gcggcagcgg cctcgtactc ggcaacccga ccgactttc cgccccggcg   1320
ggtgcgccgt acgcgcagga cccgaaccag aacccgcgcg agttccagtc gtactcgcac   1380
tacgtgatgc cgggtggtct cgtcgagtcg tttatcgatg caatcggctc gcggcgcggc   1440
ggcacgcttg cgccgaccgt caagatcaac atcaacggtg acacgacggt cgtggaccgg   1500
acgtatggca agggcggtct cggcggctac ggcgacattc ccgcaaacca gtcggcgccc   1560
ggcaatggaa acgggcaggg cggcaacagc cagtaa                             1596
```

<210> SEQ ID NO 18
<211> LENGTH: 531
<212> TYPE: PRT
<213> ORGANISM: Burkholderia phymatum STM815

<400> SEQUENCE: 18

```
Met Asn Val Gly His His Pro Arg Val Pro Arg Ile Thr Pro Arg Leu
1               5                   10                  15

Arg Ala His Phe Leu Ser Ala Ala Val Leu Ser Ala Val Ala Leu Pro
            20                  25                  30

Ala Leu Ala Gln Thr Ala Thr Pro Gly Phe Pro Ala Pro Thr Pro His
        35                  40                  45

Ser Gln Gln Ala Tyr Asp Pro Glu Ser Ser Phe Thr Met Arg Trp Thr
    50                  55                  60

Arg Ala Asp Ile Arg Gln Ile Lys Ala Gln Ser His Ala Ala Thr Ala
65                  70                  75                  80

Ala Asp Lys Asn Ser Leu Pro Leu Ser Leu Thr Met Pro Asp Ile Pro
                85                  90                  95

Gln Asp Phe Pro Leu Ile Asn Pro Asn Val Trp Val Trp Asp Thr Trp
            100                 105                 110

Pro Leu Ala Asp Met Arg Ala Asn Gln Leu Ala Tyr Lys Gly Trp Glu
        115                 120                 125

Val Ile Phe Ser Leu Thr Ala Asp Pro His Ala Gly Tyr Thr Phe Asp
    130                 135                 140

Asp Arg His Val His Ala Arg Ile Gly Phe Phe Tyr Arg Arg Ala Gly
145                 150                 155                 160

Ile Pro Ala Ser Gln Arg Pro Ala Asn Gly Gly Trp Thr Trp Gly Gly
                165                 170                 175

His Leu Phe Pro Asp Gly Ala Ser Val Lys Val Phe Gly Thr Ser Pro
            180                 185                 190

Met Thr Asp Asn Ala Glu Trp Ser Gly Ser Ala Arg Leu Thr His Gly
```

```
                195                 200                 205

Asp Asn Val Ser Leu Tyr Tyr Thr Ala Thr Ser Phe Asn Arg Ser Ala
    210                 215                 220

Pro Gly Gly Ala Asp Ile Thr Pro Gln Ala Ile Thr Arg Ala
225                 230                 235                 240

Asp Gly His Ile His Ala Asp Ser His Val Trp Phe Ser Gly Phe
                245                 250                 255

Asp Asp His Gln Ala Leu Leu Lys Pro Asp Gly Thr Tyr Tyr Gln Thr
            260                 265                 270

Gly Glu Gln Asn Thr Tyr Phe Ser Tyr Arg Asp Pro Phe Val Phe Ile
            275                 280                 285

Asp Pro Ala His Pro Gly Lys Thr Tyr Met Val Phe Glu Gly Asn Thr
        290                 295                 300

Gly Gly Pro Arg Gly Ala Arg Thr Cys Thr Glu Ala Asp Leu Gly Tyr
305                 310                 315                 320

Ala Pro Asn Asp Pro Gln Arg Glu Asp Leu Asn Ala Val Met Asn Ser
                325                 330                 335

Gly Ala Ala Tyr Gln Lys Ala Asn Val Gly Leu Ala Val Ala Thr Asn
                340                 345                 350

Pro Gln Leu Thr Glu Trp Lys Phe Leu Pro Pro Ile Leu Ser Ala Asn
            355                 360                 365

Cys Val Asp Asp Gln Thr Glu Arg Pro Gln Ile Tyr Leu Lys Asp Gly
        370                 375                 380

Lys Tyr Tyr Leu Phe Thr Ile Ser His Arg Thr Thr Met Ala Ala Gly
385                 390                 395                 400

Val Asp Gly Pro Asp Gly Val Tyr Gly Phe Val Gly Asn Gly Ile Arg
                405                 410                 415

Ser Asp Phe Leu Pro Leu Asn Gly Gly Ser Gly Leu Val Leu Gly Asn
                420                 425                 430

Pro Thr Asp Phe Ser Ala Pro Ala Gly Ala Pro Tyr Ala Gln Asp Pro
            435                 440                 445

Asn Gln Asn Pro Arg Glu Phe Gln Ser Tyr Ser His Tyr Val Met Pro
        450                 455                 460

Gly Gly Leu Val Glu Ser Phe Ile Asp Ala Ile Gly Ser Arg Arg Gly
465                 470                 475                 480

Gly Thr Leu Ala Pro Thr Val Lys Ile Asn Ile Asn Gly Asp Thr Thr
                485                 490                 495

Val Val Asp Arg Thr Tyr Gly Lys Gly Gly Leu Gly Gly Tyr Gly Asp
                500                 505                 510

Ile Pro Ala Asn Gln Ser Ala Pro Gly Asn Gly Asn Gly Gln Gly Gly
        515                 520                 525

Asn Ser Gln
    530

<210> SEQ ID NO 19
<211> LENGTH: 46
<212> TYPE: DNA
<213> ORGANISM: Artificial Sequence
<220> FEATURE:
<223> OTHER INFORMATION: forward primer

<400> SEQUENCE: 19
aaactaaaat ctaaaagatc tcagactgca acgccaggct tccccg                    46

<210> SEQ ID NO 20
```

```
<211> LENGTH: 51
<212> TYPE: DNA
<213> ORGANISM: Artificial Sequence
<220> FEATURE:
<223> OTHER INFORMATION: reverse primer

<400> SEQUENCE: 20 ggtttctttta ccagactcga gttactggct gttgccgccc tgcccgtttc c         51

<210> SEQ ID NO 21
<211> LENGTH: 1887
<212> TYPE: DNA
<213> ORGANISM: Aspergillus kawachii

<400> SEQUENCE: 21
atgaagcttc aaacggcttc cgtactgctc ggcagtgctg ctgctgcctc tccttcaatg      60
cagacgcggg cctccgtggt catcgactac aatgtcgctc ctccaaacct ctccaccctg     120
cccaatggct ccctcttcga acatggcgg ccccgcgccc acgtcctgcc cccaaacggc      180
cagatcggtg atccctgcct gcattacacc gatcccgcca cgggcctctt ccacgtcggc     240
ttccttcacg atggcagcgg catctccagt gccaccaccg atgacctagc cacctaccaa     300
gacctcaacc aaggcaacca agtcattgtc cctgggggca tcaacgaccc cgtcgctgtc     360
ttcgacggct ccgtcatccc caacggcatc aacggcctcc ccaccctcct ctacacctcc     420
gtctcctacc tccccatcca ctggtcgatc ccctacaccc gcggcagtga gactcaatcc     480
ctcgccgtct cctccgacgg cggcagcaac ttcaccaagc tcgaccaggg ccccgtcatc     540
cctggccctc ccttcgccta acgtcacc gcattccggg accccctacgt cttccaaaac     600
cccactcttg actccctcct ccacagcaag aacaacacct ggtacaccgt catctccggt     660
ggtctgcacg aaaagggccc cgctcaattc ctctaccgcc agtacgactc ggactttcag     720
tactgggagt acctcggcca atggtggcac gaacccacca actccacctg gggtaacggc     780
acctgggccg ccgctgggc cttcaacttt gagaccggca acgtcttcag tctcgacgag     840
tacggataca ccccccacgg ccagatcttc accaccatcg gcactgaggg ctctgacctg     900
cccgtcgtgc cccagctcac cagcatccac gacatgctct gggtgtccgg tacagtctct     960
cgcaatggct ctgtctcgtt caaccccaac atggcgggct cctcgactg gggcttctcc    1020
tcttacgctg ctgccggaaa ggttctcccc tcgacttctc tgccttccac gaagagcggc    1080
gccccggatc gcttcatctc ctacgtctgg ctgtccggtg acctgttcga acaggccgaa    1140
gggttcccca cgaaccagca gaattggacc ggtacgctgc tgcttccgcg tgagttgcgc    1200
gtgctgtata tccccaatgt ggtggacaat gctctggccc gggagtctgg tgcctcgtgg    1260
caggtcgtga gcagcgatgg cagtgcgggc accgtcgagc tgcagacgct gggtatctcc    1320
attgcccggg agaccaaggc cgcgttgctg tcgggaacgt cgttcactga gtccggccgc    1380
accctgaaca gcagtggtgt tgttccgttc aagcgctcgc catccgagaa gttcttcgtt    1440
ctgtccgcac agctgtcctt ccctgcttcg gctagggat cgggacttaa gagtgggttc    1500
cagatcctct catcggagca cgagagtacc actgtgtact accagttctc gaatgagtcg    1560
attatcgtgg atcgtagcaa cactagtgct gcggcgcgca cgactgatgg tatcgatagc    1620
agtgcggaag ctggcaagtt cgtctgtttt gacgtgctga atgcggcga gcaggccatt    1680
gagacgctag atttgactct cgtggtggat aactccgtgt ggaggtgta tgccaatggt    1740
cggtttcgct tgagtacctg ggttcgttcc tggtacgcca actccactaa catcagcttc    1800
ttccataatg gcgtgggtgg tgttgcgttc tccaaagtga ctgtgtccga gggcttgtat    1860
```

```
gatgcttggc cggatcgtca gtattga                                              1887
```

<210> SEQ ID NO 22
<211> LENGTH: 628
<212> TYPE: PRT
<213> ORGANISM: Aspergillus kawachii

<400> SEQUENCE: 22

| Met | Lys | Leu | Gln | Thr | Ala | Ser | Val | Leu | Leu | Gly | Ser | Ala | Ala | Ala |
|---|---|---|---|---|---|---|---|---|---|---|---|---|---|---|
| 1 | | | | 5 | | | | | 10 | | | | | 15 |

| Ser | Pro | Ser | Met | Gln | Thr | Arg | Ala | Ser | Val | Val | Ile | Asp | Tyr | Asn | Val |
|---|---|---|---|---|---|---|---|---|---|---|---|---|---|---|---|
| | | | 20 | | | | | 25 | | | | | 30 | | |

Ala Pro Pro Asn Leu Ser Thr Leu Pro Asn Gly Ser Leu Phe Glu Thr
              35                  40                  45

Trp Arg Pro Arg Ala His Val Leu Pro Pro Asn Gly Gln Ile Gly Asp
 50                  55                  60

Pro Cys Leu His Tyr Thr Asp Pro Ala Thr Gly Leu Phe His Val Gly
 65                  70                  75                  80

Phe Leu His Asp Gly Ser Gly Ile Ser Ser Ala Thr Thr Asp Asp Leu
                  85                  90                  95

Ala Thr Tyr Gln Asp Leu Asn Gln Gly Asn Gln Val Ile Val Pro Gly
              100                 105                 110

Gly Ile Asn Asp Pro Val Ala Val Phe Asp Gly Ser Val Ile Pro Asn
              115                 120                 125

Gly Ile Asn Gly Leu Pro Thr Leu Leu Tyr Thr Ser Val Ser Tyr Leu
         130                 135                 140

Pro Ile His Trp Ser Ile Pro Tyr Thr Arg Gly Ser Glu Thr Gln Ser
145                 150                 155                 160

Leu Ala Val Ser Ser Asp Gly Gly Ser Asn Phe Thr Lys Leu Asp Gln
                  165                 170                 175

Gly Pro Val Ile Pro Gly Pro Pro Phe Ala Tyr Asn Val Thr Ala Phe
              180                 185                 190

Arg Asp Pro Tyr Val Phe Gln Asn Pro Thr Leu Asp Ser Leu Leu His
         195                 200                 205

Ser Lys Asn Asn Thr Trp Tyr Thr Val Ile Ser Gly Gly Leu His Glu
     210                 215                 220

Lys Gly Pro Ala Gln Phe Leu Tyr Arg Gln Tyr Asp Ser Asp Phe Gln
225                 230                 235                 240

Tyr Trp Glu Tyr Leu Gly Gln Trp Trp His Glu Pro Thr Asn Ser Thr
                  245                 250                 255

Trp Gly Asn Gly Thr Trp Ala Gly Arg Trp Ala Phe Asn Phe Glu Thr
              260                 265                 270

Gly Asn Val Phe Ser Leu Asp Glu Tyr Gly Tyr Asn Pro His Gly Gln
         275                 280                 285

Ile Phe Thr Thr Ile Gly Thr Glu Gly Ser Asp Leu Pro Val Val Pro
     290                 295                 300

Gln Leu Thr Ser Ile His Asp Met Leu Trp Val Ser Gly Thr Val Ser
305                 310                 315                 320

Arg Asn Gly Ser Val Ser Phe Asn Pro Asn Met Ala Gly Phe Leu Asp
                  325                 330                 335

Trp Gly Phe Ser Ser Tyr Ala Ala Ala Gly Lys Val Leu Pro Ser Thr
              340                 345                 350

Ser Leu Pro Ser Thr Lys Ser Gly Ala Pro Asp Arg Phe Ile Ser Tyr
         355                 360                 365

```
Val Trp Leu Ser Gly Asp Leu Phe Glu Gln Ala Glu Gly Phe Pro Thr
    370                 375                 380

Asn Gln Gln Asn Trp Thr Gly Thr Leu Leu Leu Pro Arg Glu Leu Arg
385                 390                 395                 400

Val Leu Tyr Ile Pro Asn Val Val Asp Asn Ala Leu Ala Arg Glu Ser
                405                 410                 415

Gly Ala Ser Trp Gln Val Val Ser Ser Asp Gly Ser Ala Gly Thr Val
                420                 425                 430

Glu Leu Gln Thr Leu Gly Ile Ser Ile Ala Arg Glu Thr Lys Ala Ala
            435                 440                 445

Leu Leu Ser Gly Thr Ser Phe Thr Glu Ser Gly Arg Thr Leu Asn Ser
    450                 455                 460

Ser Gly Val Val Pro Phe Lys Arg Ser Pro Ser Glu Lys Phe Phe Val
465                 470                 475                 480

Leu Ser Ala Gln Leu Ser Phe Pro Ala Ser Ala Arg Gly Ser Gly Leu
                485                 490                 495

Lys Ser Gly Phe Gln Ile Leu Ser Ser Glu His Glu Ser Thr Thr Val
                500                 505                 510

Tyr Tyr Gln Phe Ser Asn Glu Ser Ile Ile Val Asp Arg Ser Asn Thr
            515                 520                 525

Ser Ala Ala Ala Arg Thr Thr Asp Gly Ile Asp Ser Ser Ala Glu Ala
    530                 535                 540

Gly Lys Leu Arg Leu Phe Asp Val Leu Asn Gly Glu Gln Ala Ile
545                 550                 555                 560

Glu Thr Leu Asp Leu Thr Leu Val Val Asp Asn Ser Val Leu Glu Val
                565                 570                 575

Tyr Ala Asn Gly Arg Phe Ala Leu Ser Thr Trp Val Arg Ser Trp Tyr
                580                 585                 590

Ala Asn Ser Thr Asn Ile Ser Phe Phe His Asn Gly Val Gly Gly Val
            595                 600                 605

Ala Phe Ser Lys Val Thr Val Ser Glu Gly Leu Tyr Asp Ala Trp Pro
    610                 615                 620

Asp Arg Gln Tyr
625

<210> SEQ ID NO 23
<211> LENGTH: 30
<212> TYPE: DNA
<213> ORGANISM: Artificial Sequence
<220> FEATURE:
<223> OTHER INFORMATION: forward primer

<400> SEQUENCE: 23
tctggtaaag aaaccgctgc tgcgaaattt                                       30

<210> SEQ ID NO 24
<211> LENGTH: 30
<212> TYPE: DNA
<213> ORGANISM: Artificial Sequence
<220> FEATURE:
<223> OTHER INFORMATION: reverse primer

<400> SEQUENCE: 24
tttagatttt agtttgtcac tatgatcaat                                       30

<210> SEQ ID NO 25
<211> LENGTH: 33
```

```
<212> TYPE: DNA
<213> ORGANISM: Artificial Sequence
<220> FEATURE:
<223> OTHER INFORMATION: forward primer

<400> SEQUENCE: 25
aaatctaaaa gatcctccgt ggtcatcgac tac                              33

<210> SEQ ID NO 26
<211> LENGTH: 34
<212> TYPE: DNA
<213> ORGANISM: Artificial Sequence
<220> FEATURE:
<223> OTHER INFORMATION: reverse primer

<400> SEQUENCE: 26
tttaccagac tcgagtcaat actgacgatc cggc                             34

<210> SEQ ID NO 27
<211> LENGTH: 33
<212> TYPE: DNA
<213> ORGANISM: Artificial Sequence
<220> FEATURE:
<223> OTHER INFORMATION: forward primer

<400> SEQUENCE: 27
ctcgagtctg gtaaagaaac cgctgctgcg aaa                              33

<210> SEQ ID NO 28
<211> LENGTH: 35
<212> TYPE: DNA
<213> ORGANISM: Artificial Sequence
<220> FEATURE:
<223> OTHER INFORMATION: reverse primer

<400> SEQUENCE: 28
ggatctttta gattttagtt tgtcactatg atcaa                            35

<210> SEQ ID NO 29
<211> LENGTH: 25
<212> TYPE: DNA
<213> ORGANISM: Artificial Sequence
<220> FEATURE:
<223> OTHER INFORMATION: forward primer

<400> SEQUENCE: 29
catatgcaga ctgcaacgcc aggct                                       25

<210> SEQ ID NO 30
<211> LENGTH: 28
<212> TYPE: DNA
<213> ORGANISM: Artificial Sequence
<220> FEATURE:
<223> OTHER INFORMATION: reverse primer

<400> SEQUENCE: 30
tatatctcct tcttatactt aactaata                                    28

<210> SEQ ID NO 31
<211> LENGTH: 24
<212> TYPE: DNA
<213> ORGANISM: Artificial Sequence
<220> FEATURE:
<223> OTHER INFORMATION: forward primer

<400> SEQUENCE: 31
```
catatgtccg tggtcatcga ctac                                              24

<210> SEQ ID NO 32
<211> LENGTH: 28
<212> TYPE: DNA
<213> ORGANISM: Artificial Sequence
<220> FEATURE:
<223> OTHER INFORMATION: reverse primer

<400> SEQUENCE: 32
tatatctcct tcttatactt aactaata                                          28

<210> SEQ ID NO 33
<211> LENGTH: 1197
<212> TYPE: DNA
<213> ORGANISM: Artificial Sequence
<220> FEATURE:
<223> OTHER INFORMATION: capA_opti gene

<400> SEQUENCE: 33
atgaaagaaa agaaactgaa cttccaagaa aaggtcctga tgtttattaa gaaaaccaag        60
ccgacgacgg gcaagcaagc actgattctg acgccgatcc tgattgttat cctggctctg       120
tcgggctgga tggaacgtag cgatgcgctg aaaaacccgg aaaccgccaa tccggaagca       180
aacaatgatc tgaccatgac gatggtgggc gacattatga tgggtcgtca tgtgcgcgaa       240
gttaccgaac gttatggcga agattttgtc ttccgcaacg tggaaccgtt tttcaaaaat       300
agcgactatg tgtctggtaa ctacgaaacg ccgattctga ccaatgatgt tgactcctat       360
aaaagcgatg aaaagggcat ccatctgtac tcaaaaccgg ctgatctggc gaccgtgaag       420
aatgctggtt ttgacgttct gaacctggcg aacaatcaca gtatggatta ttccgctaaa       480
ggcctggaag acacgattag cacctttgaa gcaaataagc tggatttcgt gggcgctggt       540
cgtaactctg aagaagcgaa acatatcagt tacaaggatg ccgacggcat tcgcatcgca       600
acggttggtt ttaccgatgt ccactcagac ggcatgtcgg ccgtaaaaaa caatcccggt       660
attctgaagg cagatccgga cctgattttc tcgaccatcc agcaagcaaa agctaatgcg       720
gatctggtgg ttgtcaacgc ccattggggc gaagaatatg acgcacagcc gagtccgcgc       780
caagaaggtc tggccaaagc aatggtcgat gctggcgcgg acattatcat tggtcatcac       840
ccgcacgtgc tgcagagcta tgatgtgtac aaaggtagcg ttatcttta ttctctgggc       900 aacttcatct tcgatcaggg ttggagctct acgaagaata ccgccatggt gcaataccat       960
ctgaacaaac agggccaagc taagattgat gttatcccga tggtcattaa agcgggtacc      1020
ccgacgccga ccgataatcc gtggcgtatg aaacgcatct ataacgacct gaataagttt      1080
agttccaacc cggaactgct ggaaaaagaa cgtaacaagt tcgaactgaa tctggatcat      1140
tcccgtatca ttaaacacgc ggaagaacgc aaaaagaacg aagcccaggc aaattaa        1197

<210> SEQ ID NO 34
<211> LENGTH: 398
<212> TYPE: PRT
<213> ORGANISM: Artificial Sequence
<220> FEATURE:
<223> OTHER INFORMATION: CapA protein coded by capA_opti gene

<400> SEQUENCE: 34

Met Lys Glu Lys Lys Leu Asn Phe Gln Glu Lys Val Leu Met Phe Ile
1               5                   10                  15

Lys Lys Thr Lys Pro Thr Thr Gly Lys Gln Ala Leu Ile Leu Thr Pro
            20                  25                  30

Ile Leu Ile Val Ile Leu Ala Leu Ser Gly Trp Met Glu Arg Ser Asp
        35                  40                  45

Ala Leu Glu Asn Pro Glu Thr Ala Asn Pro Glu Ala Asn Asn Asp Leu
    50                  55                  60

Thr Met Thr Met Val Gly Asp Ile Met Met Gly Arg His Val Arg Glu
65                  70                  75                  80

Val Thr Glu Arg Tyr Gly Glu Asp Phe Val Phe Arg Asn Val Glu Pro
                85                  90                  95

Phe Phe Lys Asn Ser Asp Tyr Val Ser Gly Asn Tyr Glu Thr Pro Ile
            100                 105                 110

Leu Thr Asn Asp Val Asp Ser Tyr Lys Ala Met Glu Lys Gly Ile His
        115                 120                 125

Leu Tyr Ser Lys Pro Ala Asp Leu Ala Thr Val Lys Asn Ala Gly Phe
    130                 135                 140

Asp Val Leu Asn Leu Ala Asn Asn His Ser Met Asp Tyr Ser Ala Lys
145                 150                 155                 160

Gly Leu Glu Asp Thr Ile Ser Thr Phe Glu Ala Asn Lys Leu Asp Phe
                165                 170                 175

Val Gly Ala Gly Arg Asn Ser Glu Glu Ala Lys His Ile Ser Tyr Lys
            180                 185                 190

Asp Ala Asp Gly Ile Arg Ile Ala Thr Val Gly Phe Thr Asp Val His
        195                 200                 205

Ser Asp Gly Met Ser Ala Gly Lys Asn Asn Pro Gly Ile Leu Lys Ala
    210                 215                 220

Asp Pro Asp Leu Ile Phe Ser Thr Ile Gln Ala Lys Ala Asn Ala
225                 230                 235                 240

Asp Leu Val Val Val Asn Ala His Trp Gly Glu Glu Tyr Asp Ala Gln
                245                 250                 255

Pro Ser Pro Arg Gln Glu Gly Leu Ala Lys Ala Met Val Asp Ala Gly
            260                 265                 270

Ala Asp Ile Ile Ile Gly His His Pro His Val Leu Gln Ser Tyr Asp
        275                 280                 285

Val Tyr Lys Gly Ser Val Ile Phe Tyr Ser Leu Gly Asn Phe Ile Phe
    290                 295                 300

Asp Gln Gly Trp Ser Ser Thr Lys Asn Thr Ala Met Val Gln Tyr His
305                 310                 315                 320

Leu Asn Lys Gln Gly Gln Ala Lys Ile Asp Val Ile Pro Met Val Ile
                325                 330                 335

Lys Ala Gly Thr Pro Thr Pro Thr Asp Asn Pro Trp Arg Met Lys Arg
            340                 345                 350

Ile Tyr Asn Asp Leu Asn Lys Phe Ser Ser Pro Glu Leu Leu Glu
        355                 360                 365

Lys Glu Arg Asn Lys Phe Glu Leu Asn Leu Asp His Ser Arg Ile Ile
    370                 375                 380

Lys His Ala Glu Glu Arg Lys Lys Asn Glu Ala Gln Ala Asn
385                 390                 395

<210> SEQ ID NO 35
<211> LENGTH: 46
<212> TYPE: DNA
<213> ORGANISM: Artificial Sequence
<220> FEATURE:
<223> OTHER INFORMATION: forward primer

<400> SEQUENCE: 35

```
taagaaggag atatacatat gaaagaaaag aaactgaact tccaag          46
```

<210> SEQ ID NO 36
<211> LENGTH: 46
<212> TYPE: DNA
<213> ORGANISM: Artificial Sequence
<220> FEATURE:
<223> OTHER INFORMATION: reverse primer

<400> SEQUENCE: 36

```
cgggtaaccc gattgagatc tatttgcctg ggcttcgttc tttttg          46
```

<210> SEQ ID NO 37
<211> LENGTH: 1170
<212> TYPE: DNA
<213> ORGANISM: Brevibacillus brevis

<400> SEQUENCE: 37

```
atgaacgaga acagatcaag ccggatacat gctcggcgca aacgctcacg cagaaaatgg    60
gcacgtgtgg gaaagagcac gctcctcttt agcctgttgg ccatcttcgt cgtcggaacc   120
tactacttat ttcaaactgc catggatgga aacatgcca  acccgaacac ccagcctgct   180
cctgatgata ccgcgaacca aaagtcttcc gtgcagctca cctttgtcgg tgacatcatg   240
atgtcaggaa acgttgagaa aaccttactt gcaaacagct atgactaccc atacaaacat   300
gtaagctcgc tcttttttgca agatgatatc accattgcca atttggagac gccgatcacc   360
gacacaggtg ttgctgctca aaacaaggag tatgtttaca agtcatcgcc acttgctgtt   420
cctgccatga aaaacgctgg gattgatgtg gtgaatctgg ccaataacca ctccatggac   480
caaggcgttc cgggattgct ggatacccttt gaagctttgg acgaaaaccg tatagaatac   540
gtcggtgccg gtaaggatgc aagccgtgcc tattcacctg ttttcctaga aaagaacggc   600
atcaagatcg cgattctcgg cttcagcagg gtcattcccg aaacgagctg gtttgcaggg   660
aattcccagc caggtatggc cgcttcctat gatcctacac tggcagtgaa agcgatccag   720
gatgcgaaca gccaagcgga tctcgtggtg gtgattgcac actggggcaa agaacgctcc   780
gattatcctg tcgatcatca aaaggagctg tctcgtgcct acatcgatgc tggtgcagat   840
ttgattgtcg gcggtcatcc ccacgtactg caaggctttg aacgttacaa cgacaaatgg   900
attgcgtaca gtcttggcaa tttcatttc acacgtgcaa acgaacccaa gacttgggaa   960
acgatggtcc tacaagcaaa ctgctccaaa agtggtgatt gtgagctaac gatgcttcca  1020
tttcatgcag aattaggaca gctgtaccc atgaatgaaa gcaacggcgc tgccctgtta  1080
aaacgcattg aatccatttc tgagcaagtc gacatacaaa gtgacggacg tgtgcagcca  1140
catgcaaagg cggtggagac tgcccctga                                    1170
```

<210> SEQ ID NO 38
<211> LENGTH: 389
<212> TYPE: PRT
<213> ORGANISM: Brevibacillus brevis

<400> SEQUENCE: 38

```
Met Asn Glu Asn Arg Ser Ser Arg Ile His Ala Arg Arg Lys Arg Ser
 1               5                  10                  15

Arg Arg Lys Trp Ala Arg Val Gly Lys Ser Thr Leu Leu Phe Ser Leu
            20                  25                  30

Leu Ala Ile Phe Val Val Gly Thr Tyr Tyr Leu Phe Gln Thr Ala Met
        35                  40                  45
```

Asp Gly Glu His Ala Asn Pro Asn Thr Gln Pro Ala Pro Asp Asp Thr
 50                  55                  60

Ala Asn Gln Lys Ser Ser Val Gln Leu Thr Phe Val Gly Asp Ile Met
 65                  70                  75                  80

Met Ser Gly Asn Val Glu Lys Thr Leu Leu Ala Asn Ser Tyr Asp Tyr
                 85                  90                  95

Pro Tyr Lys His Val Ser Ser Leu Phe Leu Gln Asp Asp Ile Thr Ile
                100                 105                 110

Ala Asn Leu Glu Thr Pro Ile Thr Asp Thr Gly Val Ala Ala Gln Asn
            115                 120                 125

Lys Glu Tyr Val Tyr Lys Ser Ser Pro Leu Ala Val Pro Ala Met Lys
            130                 135                 140

Asn Ala Gly Ile Asp Val Val Asn Leu Ala Asn Asn His Ser Met Asp
145                 150                 155                 160

Gln Gly Val Pro Gly Leu Leu Asp Thr Phe Glu Ala Leu Asp Glu Asn
                165                 170                 175

Arg Ile Glu Tyr Val Gly Ala Gly Lys Asp Ala Ser Arg Ala Tyr Ser
                180                 185                 190

Pro Val Phe Leu Glu Lys Asn Gly Ile Lys Ile Ala Ile Leu Gly Phe
                195                 200                 205

Ser Arg Val Ile Pro Glu Thr Ser Trp Phe Ala Gly Asn Ser Gln Pro
210                 215                 220

Gly Met Ala Ala Ser Tyr Asp Pro Thr Leu Ala Val Lys Ala Ile Gln
225                 230                 235                 240

Asp Ala Asn Ser Gln Ala Asp Leu Val Val Ile Ala His Trp Gly
                245                 250                 255

Lys Glu Arg Ser Asp Tyr Pro Val Asp His Gln Lys Glu Leu Ser Arg
                260                 265                 270

Ala Tyr Ile Asp Ala Gly Ala Asp Leu Ile Val Gly His Pro His
                275                 280                 285

Val Leu Gln Gly Phe Glu Arg Tyr Asn Asp Lys Trp Ile Ala Tyr Ser
290                 295                 300

Leu Gly Asn Phe Ile Phe Thr Arg Ala Asn Glu Pro Lys Thr Trp Glu
305                 310                 315                 320

Thr Met Val Leu Gln Ala Asn Cys Ser Lys Ser Gly Asp Cys Glu Leu
                325                 330                 335

Thr Met Leu Pro Phe His Ala Glu Leu Gly Gln Ala Val Pro Met Asn
                340                 345                 350

Glu Ser Asn Gly Ala Ala Leu Leu Lys Arg Ile Glu Ser Ile Ser Glu
                355                 360                 365

Gln Val Asp Ile Gln Ser Asp Gly Arg Val Gln Pro His Ala Lys Ala
            370                 375                 380

Val Glu Thr Ala Pro
385

<210> SEQ ID NO 39
<211> LENGTH: 35
<212> TYPE: DNA
<213> ORGANISM: Artificial Sequence
<220> FEATURE:
<223> OTHER INFORMATION: forward primer

<400> SEQUENCE: 39
gaaggagata tacatatgaa cgagaacaga tcaag         35

```
<210> SEQ ID NO 40
<211> LENGTH: 33
<212> TYPE: DNA
<213> ORGANISM: Artificial Sequence
<220> FEATURE:
<223> OTHER INFORMATION: reverse primer

<400> SEQUENCE: 40
gtaacccgag gatctggggg cagtctccac cgc                                33

<210> SEQ ID NO 41
<211> LENGTH: 29
<212> TYPE: DNA
<213> ORGANISM: Artificial Sequence
<220> FEATURE:
<223> OTHER INFORMATION: forward primer

<400> SEQUENCE: 41
agatctcaat cgggttaccc gataccgac                                     29

<210> SEQ ID NO 42
<211> LENGTH: 29
<212> TYPE: DNA
<213> ORGANISM: Artificial Sequence
<220> FEATURE:
<223> OTHER INFORMATION: reverse primer

<400> SEQUENCE: 42
catatgtata tctccttctt atacttaac                                     29

<210> SEQ ID NO 43
<211> LENGTH: 25
<212> TYPE: DNA
<213> ORGANISM: Artificial Sequence
<220> FEATURE:
<223> OTHER INFORMATION: forward primer

<400> SEQUENCE: 43
agatcctcgg gttacccgat accga                                         25

<210> SEQ ID NO 44
<211> LENGTH: 27
<212> TYPE: DNA
<213> ORGANISM: Artificial Sequence
<220> FEATURE:
<223> OTHER INFORMATION: reverse primer

<400> SEQUENCE: 44
atgtatatct ccttcttata cttaact                                       27

<210> SEQ ID NO 45
<211> LENGTH: 40
<212> TYPE: DNA
<213> ORGANISM: Artificial Sequence
<220> FEATURE:
<223> OTHER INFORMATION: forward primer

<400> SEQUENCE: 45
aaggaggaag gatcaatgaa aaaagaactg agctttcatg                         40

<210> SEQ ID NO 46
<211> LENGTH: 40
<212> TYPE: DNA
<213> ORGANISM: Artificial Sequence
<220> FEATURE:
<223> OTHER INFORMATION: reverse primer
```

<400> SEQUENCE: 46
cccggggacg tcgacttact ggccgttcgt gacaccatgg          40

<210> SEQ ID NO 47
<211> LENGTH: 30
<212> TYPE: DNA
<213> ORGANISM: Artificial Sequence
<220> FEATURE:
<223> OTHER INFORMATION: forward primer

<400> SEQUENCE: 47
gtcgacgtcc ccggggcagc ccgcctaatg                    30

<210> SEQ ID NO 48
<211> LENGTH: 30
<212> TYPE: DNA
<213> ORGANISM: Artificial Sequence
<220> FEATURE:
<223> OTHER INFORMATION: reverse primer

<400> SEQUENCE: 48
tgatccttcc tcctttaatt gggaattgtt                    30

<210> SEQ ID NO 49
<211> LENGTH: 40
<212> TYPE: DNA
<213> ORGANISM: Artificial Sequence
<220> FEATURE:
<223> OTHER INFORMATION: forward primer

<400> SEQUENCE: 49 aggggggaaat gacaaatgaa agaaaagaaa ctgaacttcc        40

<210> SEQ ID NO 50
<211> LENGTH: 40
<212> TYPE: DNA
<213> ORGANISM: Artificial Sequence
<220> FEATURE:
<223> OTHER INFORMATION: reverse primer

<400> SEQUENCE: 50
actagtttgg accatttact ggccgttcgt gacaccatgg         40

<210> SEQ ID NO 51
<211> LENGTH: 30
<212> TYPE: DNA
<213> ORGANISM: Artificial Sequence
<220> FEATURE:
<223> OTHER INFORMATION: forward primer

<400> SEQUENCE: 51
atggtccaaa ctagtactaa taaaattaat                    30

<210> SEQ ID NO 52
<211> LENGTH: 30
<212> TYPE: DNA
<213> ORGANISM: Artificial Sequence
<220> FEATURE:
<223> OTHER INFORMATION: reverse primer

<400> SEQUENCE: 52
ttgtcatttc cccctttgat ttaagtgaac                    30